United States Patent
Smith et al.

(10) Patent No.: US 10,682,369 B2
(45) Date of Patent: Jun. 16, 2020

(54) 4'-FLUORO-2'-METHYL SUBSTITUTED NUCLEOSIDE DERIVATIVES AS INHIBITORS OF HCV RNA REPLICATION

(71) Applicant: Riboscience LLC, Sunnyvale, CA (US)

(72) Inventors: Mark Smith, Sunnyvale, CA (US); Klaus G. Klumpp, Sunnyvale, CA (US)

(73) Assignee: Riboscience LLC, Palo Alto, CA (US)

(*) Notice: Subject to any disclaimer, the term of this patent is extended or adjusted under 35 U.S.C. 154(b) by 0 days.

(21) Appl. No.: 16/138,698

(22) Filed: Sep. 21, 2018

(65) Prior Publication Data

US 2019/0231804 A1    Aug. 1, 2019

Related U.S. Application Data

(60) Provisional application No. 62/561,237, filed on Sep. 21, 2017.

(51) Int. Cl.

| A61K 31/7068 | (2006.01) |
|---|---|
| A61K 31/7072 | (2006.01) |
| C07H 19/10 | (2006.01) |
| A61P 31/14 | (2006.01) |
| A61K 45/06 | (2006.01) |

(52) U.S. Cl.
CPC ...... *A61K 31/7068* (2013.01); *A61K 31/7072* (2013.01); *A61K 45/06* (2013.01); *A61P 31/14* (2018.01); *C07H 19/10* (2013.01)

(58) Field of Classification Search
None
See application file for complete search history.

(56) References Cited

U.S. PATENT DOCUMENTS

| 4,147,864 | A | 4/1979 | Woodward et al. |
|---|---|---|---|
| 4,322,347 | A | 3/1982 | Cundall et al. |
| 5,807,876 | A | 9/1998 | Armistead et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 7,429,572 | B2 | 9/2008 | Clark |
| 7,964,580 | B2 | 6/2011 | Sofia et al. |
| 8,173,621 | B2 | 5/2012 | Du et al. |
| 8,334,270 | B2 | 12/2012 | Sofia et al. |
| 8,415,322 | B2 | 4/2013 | Clark |
| 8,580,765 | B2 | 11/2013 | Sofia et al. |
| 8,735,372 | B2 | 5/2014 | Du et al. |
| 8,759,510 | B2 | 6/2014 | Du et al. |
| 9,895,442 | B2 | 2/2018 | Smith et al. |
| 2003/0170891 | A1 | 9/2003 | McSwiggen |
| 2003/0175950 | A1 | 9/2003 | McSwiggen |
| 2005/0020884 | A1 | 1/2005 | Hart et al. |
| 2007/0042988 | A1 | 2/2007 | Klumpp et al. |
| 2010/0016251 | A1 | 1/2010 | Sofia et al. |
| 2012/0232029 | A1 | 9/2012 | Sofia et al. |
| 2012/0316327 | A1 | 12/2012 | Chun et al. |
| 2013/0315867 | A1 | 11/2013 | Parsy et al. |
| 2014/0178338 | A1 | 6/2014 | Mayes et al. |
| 2014/0179627 | A1 | 6/2014 | Beigelman et al. |
| 2014/0341847 | A1* | 11/2014 | Smith ............... A61K 31/7072 424/85.4 |
| 2016/0115186 | A1 | 4/2016 | Wang et al. |
| 2018/0200280 | A1 | 7/2018 | Smith et al. |

FOREIGN PATENT DOCUMENTS

| BE | 875247 A | 10/1979 |
|---|---|---|
| CN | 101918425 A | 12/2010 |
| CN | 102325783 A | 1/2012 |
| CN | 104011061 A | 8/2014 |
| CN | 105073766 A | 11/2015 |
| DE | 2506330 A1 | 9/1975 |
| GB | 1503581 A | 3/1978 |
| WO | WO-86/06380 A1 | 11/1986 |
| WO | WO-97/40028 A1 | 10/1997 |
| WO | WO-98/17679 A1 | 4/1998 |
| WO | WO-98/22496 A2 | 5/1998 |
| WO | WO-98/40381 A1 | 9/1998 |
| WO | WO-99/01582 A1 | 1/1999 |
| WO | WO-99/07734 A2 | 2/1999 |
| WO | WO-00/06529 A1 | 2/2000 |
| WO | WO-00/09543 A2 | 2/2000 |
| WO | WO-00/10573 A1 | 3/2000 |
| WO | WO-00/13708 A1 | 3/2000 |
| WO | WO-00/18231 A1 | 4/2000 |
| WO | WO-00/56331 A1 | 9/2000 |

(Continued)

OTHER PUBLICATIONS

Summa, Antimicrobial Agents and Chemotherapy, vol. 56, No. 8, pp. 4161-4167, Aug. 2012. (Year: 2012).*

(Continued)

*Primary Examiner* — Layla D Berry
(74) *Attorney, Agent, or Firm* — Mintz Levin Cohn Ferris Glovsky and Popeo, P.C.

(57) ABSTRACT

Cytidine nucleoside analogues of Formula I, wherein the variables are as described herein, in combination with uridine nucleoside analogues of Formula II, wherein the variables are as described herein,

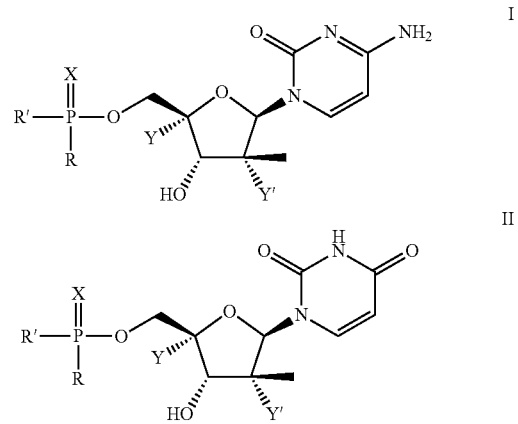

produce a synergistic effect on the inhibition of HCV polymerase.

22 Claims, No Drawings

(56) References Cited

FOREIGN PATENT DOCUMENTS

| | | | |
|---|---|---|---|
| WO | WO-01/32153 A2 | 5/2001 | |
| WO | WO-01/085172 A1 | 11/2001 | |
| WO | WO-02/04425 A2 | 1/2002 | |
| WO | WO-02/18369 A2 | 3/2002 | |
| WO | WO-02/100846 A1 | 12/2002 | |
| WO | WO-02/100851 A2 | 12/2002 | |
| WO | WO-03/000254 A1 | 1/2003 | |
| WO | WO-03/007945 A1 | 1/2003 | |
| WO | WO-03/010141 A2 | 2/2003 | |
| WO | WO-03/037893 A1 | 5/2003 | |
| WO | WO-03/037894 A1 | 5/2003 | |
| WO | WO-03/037895 A1 | 5/2003 | |
| WO | WO-2004/000858 A2 | 12/2003 | |
| WO | WO-2004/096235 A2 | 11/2004 | |
| WO | WO-2004/099241 A1 | 11/2004 | |
| WO | WO-2005/007810 A2 | 1/2005 | |
| WO | WO-2005/012327 A2 | 2/2005 | |
| WO | WO-2005/020884 A2 | 3/2005 | |
| WO | WO-2005/073195 A2 | 8/2005 | |
| WO | WO-2005/073216 A2 | 8/2005 | |
| WO | WO-2006/063281 A2 | 6/2006 | |
| WO | WO-2007/095269 A2 | 8/2007 | |
| WO | WO-2007095269 A2 * | 8/2007 | ............ C07H 19/06 |
| WO | WO-2008/017507 A2 | 2/2008 | |
| WO | WO-2008/021927 A2 | 2/2008 | |
| WO | WO-2008/085508 A2 | 7/2008 | |
| WO | WO-2008/121634 A2 | 10/2008 | |
| WO | WO-2008/142055 A2 | 11/2008 | |
| WO | WO-2009/152095 A2 | 12/2009 | |
| WO | WO-2010/075554 A1 | 7/2010 | |
| WO | WO-2011/133871 A2 | 10/2011 | |
| WO | WO-2012/012465 A1 | 1/2012 | |
| WO | WO-2012/040127 A1 | 3/2012 | |
| WO | WO-2013/019874 A9 | 2/2013 | |
| WO | WO-2013/092481 A1 | 6/2013 | |
| WO | WO-2013142159 A1 * | 9/2013 | ......... A61K 31/4178 |
| WO | WO-2014/099941 A1 | 6/2014 | |
| WO | WO-2014/100505 A1 | 6/2014 | |
| WO | WO-2014/186637 | 11/2014 | |
| WO | WO-2014/186637 A1 | 11/2014 | |
| WO | WO-2016/035006 A1 | 3/2016 | |
| WO | WO-2019/060740 A1 | 3/2019 | |

OTHER PUBLICATIONS

Bhatia, J Pharmacol Pharmacother. Oct.-Dec. 2014; 5(4): 278-284. (Year: 2014).*

Ajmera, S. et al. (Jun. 1988). "Synthesis and interaction with uridine phosphorylase of 5'-deoxy-4',5-difluorouridine, a new prodrug of 5-fluorouracil," *J Med Chem* 31(6):1094-1098.

Clark, et al, Design, Synthesis, and Antiviral Activity of 2'-Deoxy-2'-fluoro-2'-C-methylcytidine, a Potent Inhibitor of Hepatitis C Virus Replication, J. Med. Chem. 2005 vol. 48(17) pp. 5504-5508.

Congiatu et al., Naphthyl phosphoramidate derivatives of BvdU as potential anticancer agents: design, synthesis and biological evaluation, Nucleosides, Nucleotides, and Nucleic Acids, vol. 24(5-7), pp. 485-489, 2005.

Feng et al., Role of Mitochondrial RNA Polymerase in the Toxicity of Nucleotide Inhibitors of Hepatitis C Virus, Antimicrobial Agents and Chemotherapy, 2016, pp. 806-817, vol. 60.

Gish, R.G. (1999). Standards of treatment in chronic hepatitis C, *Semin Liver Dis* 19 Suppl 1:35-47.

Jenkins, I.D. et al. (Aug. 25, 1971). "Synthesis of the nucleoside antibiotic nucleocidin," *J Am Chem Soc* 93(17):4323-4324.

Krieger, N. et al. (May 2001). "Enhancement of hepatitis C virus RNA replication by cell culture-adaptive mutations," *J Virol* 75(10):4614-4624.

Kubo, A. et al. (1987). "Preparations and Reactions of (Z)-3-Arylidene-6-arylmethyl-2, 5-*piperazinediones Having Highly Oxygenated Benzene Rings,"* Chemical and Pharmaceutical Bulletin 35(6):2525-2532.

Lohmann, V. et al. (Jul. 2, 1999). "Replication of subgenomic hepatitis C virus RNAs in a hepatoma cell line," *Science* 285(5424):110-113.

Ma et al., Characterization of the Metabolic Activation of Hepatitis C Virus Nucleoside Inhibitor β-D-2'-Deoxy-2'-fluoro-2'-C-methylcytidine (PSI-6130) and Identification of a Novel Active 5'-Triophosphate Species*, The Journal of Biological Chemistry, 2007, pp. 29812-29820, vol. 282:41, JBC Papers in Press.

McGuigan et al., Phosphoramidate ProTides of 2"-C-Methylguanosine as Highly Potent Inhibitors of Hepatitis C Virus. Study of Their in Vitro and in Vivo Properties, J. Med. Chem, vol. 53, pp. 4949-4957, 2010.

Ryan, M.D. et al. (Feb. 15, 1994). "Foot-and-mouth disease virus 2A oligopeptide mediated cleavage of an artificial polyprotein," *EMBO J* 13(4):928-933.

Sofia et al., Discovery of a β-D-2'-Deoxy-2'β-C-methyluridine Nucleotide Prodrug (PSI-7977) for the Treatment of Hepatitis C Virus, J. Med. Chem, vol. 53(19), pp. 7202-7218, 2010.

International Search Report dated Mar. 7, 2019, for PCT Application No. PCT/US2018/052239, filed Mar. 7, 2019, 4 pages.

Written Opinion dated Mar. 7, 2019, for PCT Application No. PCT/US2018/052239, filed Mar. 7, 2019, 5 pages.

Anonymous Third-Party Observations filed in PCT International Application No. PCT/US2018/052239 dated Jan. 21, 2020 (6 pages).

Sofia, "Nucleotide Prodrugs for the Treatment of HCV Infection," Advances in Pharmacology: Antiviral Agents, 67, pp. 39-73 (2013).

* cited by examiner

4'-FLUORO-2'-METHYL SUBSTITUTED NUCLEOSIDE DERIVATIVES AS INHIBITORS OF HCV RNA REPLICATION

CROSS REFERENCES TO RELATED APPLICATIONS

This application claims the benefit of priority under 35 U.S. § 119(e) to U.S. Provisional Application Ser. No. 62/561,237 filed Sep. 21, 2017, the disclosure of which is incorporated herein by reference in its entirety.

FIELD OF THE INVENTION

The invention relates to combinations of nucleoside derivatives as inhibitors of HCV replicon RNA replication. In particular, the invention is concerned with the use of combinations of cytidine and uridine pyrimidine nucleoside derivatives as inhibitors of subgenomic hepatitis C virus (HCV) RNA replication and pharmaceutical compositions containing such compounds. In particular, the cytidine nucleoside analogues of Formula I, in combination with the uridine nucleoside analogues of Formula II, produce a synergistic effect on the inhibition of HCV polymerase.

BACKGROUND OF THE INVENTION

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, Sem. Liver. Dis., 1999, 19, 35). These are interferon-α monotherapy and, more recently, combination therapy of the nucleoside analogue, ribavirin (Virazole), with interferon-α.

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. This conversion to the triphosphate is commonly mediated by cellular kinases and therefore the direct evaluation of nucleosides as inhibitors of HCV replication is only conveniently carried out using a cell-based assay. For HCV the availability of a true cell-based viral replication assay or animal model of infection is lacking.

Hepatitis C virus belongs to the family of Flaviridae. It is an RNA virus, the RNA genome encoding a large polyprotein which after processing produces the necessary replication machinery to ensure synthesis of progeny RNA. It is believed that most of the non-structural proteins encoded by the HCV RNA genome are involved in RNA replication. Lohmann et al. [V. Lohmann et al., Science, 1999, 285, 110-113] have described the construction of a Human Hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

SUMMARY OF THE INVENTION

In a first aspect, provided are methods of treatment of HCV by administering to a patient in need thereof a combination of a compound of Formula I and a compound of Formula II:

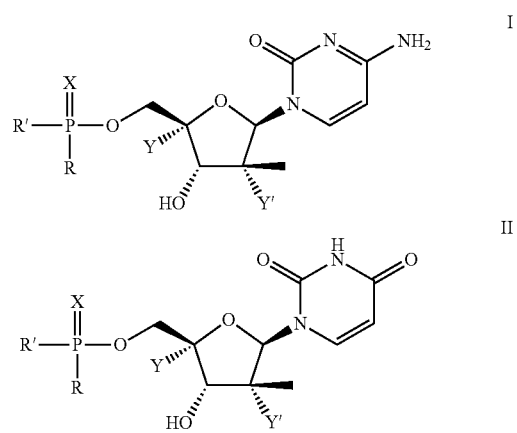

wherein:
each R is independently O—$R^1$ or NHC($R^{2a}$)($R^{2b}$)C(=O)O$R^3$;
each R' is independently O—$R^1$ or NHC($R^{2a}$)($R^{2b}$)C(=O)O$R^3$;
each $R^1$ is independently phenyl or naphthyl, optionally substituted with one or more lower alkyl, lower alkoxy, halo, lower haloalkyl, or cyano;
each $R^{2a}$ and $R^{2b}$ are independently H or lower alkyl;
each $R^3$ is independently H, lower alkyl, lower haloalkyl, cycloalkyl, phenyl or phenyl lower alkyl;
each X is independently O or S;
each Y is independently H or F; and
each Y' is independently F or OH;
or a pharmacologically acceptable salt thereof (or any embodiments thereof disclosed herein).

In a second aspect, provided are compounds of Formula I selected from:
isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;
isopropyl ((R)-(((2S,3 S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;
isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
pentan-3-yl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
diisopropyl (((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

pentan-3-yl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate;

isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate;

isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate;

isopropyl ((R)-(((2S,3 S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

pentan-3-yl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

cyclohexyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

pentan-3-yl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

((2S,3S,4R,5R)-5-(4-amino-2-oxopyrimidin-1(2H)-yl)-2-fluoro-3,4-dihydroxy-4-methyltetrahydrofuran-2-yl) methyl diphenyl phosphate;

isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate; and isopropyl ((R)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate; and a mixture of $S_P$ and $R_P$ epimers thereof; or a pharmaceutically acceptable salt of each of the foregoing compound.

In a third aspect, provided are compounds also provided is a compound of Formula III:

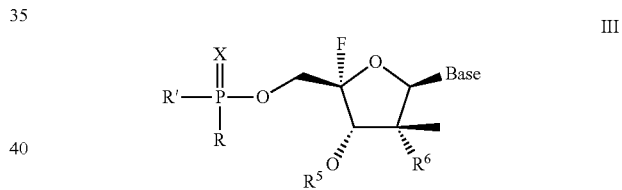

III wherein:
R is O—$R^1$ or NH$R^{1'}$;
or R and $R^5$ together form a bond;
R' is N($R^4$)C($R^{2a}$)($R^{2b}$)C(=O)O$R^3$ or —O$R^3$;
$R^1$ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —COR$^{1b}$, —SO$_2$($R^{1c}$), —NHSO$_2$($R^{1c}$), nitro or cyano;
each $R^{1a}$ is independently H or lower alkyl;
each $R^{1b}$ is independently —O$R^{1a}$ or —N($R^{1a}$)$_2$;
each $R^{1c}$ is lower alkyl;
$R^{1''}$ is —C($R^{2a}$)($R^{2b}$)C(=O)O$R^3$;
each $R^{2a}$ and $R^{2b}$ are independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_3$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl may optionally be substituted with one or more hydroxy, lower alkyl, lower alkoxy, halo, nitro or cyano;
or $R^{2a}$ is H and $R^{2b}$ and $R^4$ together form (CH$_2$)$_n$;
each $R^3$ is H, lower alkyl, lower haloalkyl, phenyl or phenyl lower alkyl;

each $R^4$ is H, lower alkyl, or $R^{2b}$ and $R^4$ together form $(CH_2)_3$;

$R^5$ is H, $C(=O)R^{1c}$, $C(=O)R^{1b}$, $P(=O)(OR^1)(OR^{1a})$, or $P(=O)(OR^1)(NR^4R^7)$;

$R^6$ is OH or F;

$R^7$ is $C(R^{2a}R^{2b})C(=O)OR^3$ m is 0 to 3;

n is 3, 4 or 5;

p is 0 to 2;

r is 1 to 6;

X is O or S; and

Base is uracil, cytosine, guanine, adenine, thymine, or heterocycloalkyl, each of which may optionally substituted with one or more hydroxy, lower alkyl, lower alkoxy, halo, nitro or cyano;

or a pharmacologically acceptable salt thereof.

The compounds of Formulae I, II, and III are useful for the treatment of diseases mediated by the hepatitis C virus (HCV).

The application also provides a method for treating a hepatitis C virus (HCV) infection comprising administering to a patient in need thereof a therapeutically effective amount of a compound of Formula III.

The application further provides a composition comprising a compound of Formulae I, II, and III and a pharmaceutically acceptable excipient.

DETAILED DESCRIPTION OF THE INVENTION

The compounds of Formulae I and II have been shown to be inhibitors of subgenomic hepatitis C virus replication in a hepatoma cell line. These compounds should be efficacious as antiviral drugs for the treatment of HCV infections in human.

Definitions

Unless stated otherwise, the following terms used in the claims and the specification have the meaning below.

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms and may be referred to herein as lower alkyl. Most preferred are methyl, ethyl, propyl, isopropyl, n-butyl, isobutyl, tert.-butyl or pentyl. The alkyl may be unsubstituted or substituted. The substituents are selected from one or more of cycloalkyl, nitro, amino, alkylamino, dialkylamino, alkylcarbonyl and cycloalkylcarbonyl. In one embodiment, alkyl is unsubstituted.

The term "cycloalkyl" as used herein denotes an optionally substituted cycloalkyl group containing 3 to 7 carbon atoms, e.g. cyclopropyl, cyclobutyl, cyclopentyl, cyclohexyl or cycloheptyl. The substituents are selected from one or more of cycloalkyl, nitro, amino, alkylamino, dialkylamino, alkylcarbonyl and cycloalkylcarbonyl. In one embodiment, cycloalkyl is unsubstituted.

The term "cycloalkylcarbonyl as used herein denotes a group of formula —C(=O)R wherein R is cycloalkyl as defined above.

The term "alkoxy" as used herein denotes an optionally substituted straight or branched chain alkyl-oxy group wherein the "alkyl", including lower alkyl, portion is as defined above. Examples include, and are not limited to, methoxy, ethoxy, n-propyloxy, i-propyloxy, n-butyloxy, i-butyloxy, tert.-butyloxy, pentyloxy, hexyloxy, heptyloxy including their isomers.

The term "alkylamino" as used herein denotes straight or branched chain alkyl-NH-group wherein the "alkyl", including lower alkyl, portion is as defined above.

The term "dialkylamino" as used herein denotes straight or branched chain $(alkyl)_2$-N-group wherein the "alkyl", including lower alkyl, portion is as defined above.

The term "alkoxyalkyl" as used herein denotes an alkoxy group as defined above which is bonded to an alkyl, including lower alkyl, group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert.-butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Alkenyl containing 2 to 4 carbon atoms may be referred to herein as lower alkenyl. The substituents are selected from one or more of cycloalkyl, nitro, amino, alkylamino, dialkylamino, alkylcarbonyl and cycloalkylcarbonyl. In one embodiment, alkenyl is unsubstituted. Examples are vinyl, 1-propenyl, 2-propenyl (allyl) or 2-butenyl (crotyl).

The term "alkynyl" as used herein denotes to unsubstituted or substituted hydrocarbon chain radical having from 2 to 7 carbon atoms, preferably 2 to 4 carbon atoms, and having one or where possible two triple bonds, preferably one triple bond. Alkynyl containing 2 to 4 carbon atoms may be referred to herein as lower alkynyl. The substituents are selected from one or more of cycloalkyl, nitro, amino, alkylamino, dialkylamino, alkylcarbonyl and cycloalkylcarbonyl. In one embodiment, alkyl is unsubstituted. Examples are ethynyl, 1-propynyl, 2-propynyl, 1-butynyl, 2-butynyl or 3-butynyl.

The term "hydroxyalkyl" as used herein denotes a straight or branched chain alkyl group, including lower alkyl group, as defined above, wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group, including lower alkyl group, as defined above, wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "aryl" as used herein denotes an optionally substituted phenyl and naphthyl (e.g. 1-naphthyl, 2-naphthyl or 3-naphthyl) unless stated otherwise. Suitable substituents for aryl can be selected from those named for alkyl, in addition however, halogen, hydroxy, alkoxy, and optionally substituted alkyl (i.e., alkyl that is unsubstituted or substituted as defined above), haloalkyl, alkenyl, alkynyl and aryloxy are substituents which can be added to the selection. In one embodiment, the substituents include other than alkoxy.

The term "arylalkyl" as used herein denotes aryl attached to an alkyl, each term as defined above. When aryl is phenyl, it can also be referred to herein as phenylalkyl.

The term "heterocyclyl" or "heterocycloalkyl" as used herein denotes an optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle. Suitable substituents for heterocyclyl can be selected from those named for alkyl, in addition however, optionally substituted alkyl, alkenyl, alkynyl, an oxo group (=O) or aminosulphonyl (—SO$_2$NH$_2$) are substituents which can be added to the selection. Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e.g. 1,2,3-triazolyl or 1,2,4-triazolyl, 1-pyrazolyl, 2-pyrazolyl, 4-pyrazolyl, piperidinyl, morpholinyl (e.g. 4-morpholinyl), thiomorpholinyl (e.g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e.g. 1,2,3-thiadiazolyl, 4-methylpiperazinyl, 4-hydroxypiperidin-1-yl.

The term "acyl" ("alkylcarbonyl") as used herein denotes a group of formula C(=O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term "acylamino" as used herein denotes a group of formula —NHC(=O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term halogen or halo stands for fluorine, chlorine, bromine or iodine, preferable fluorine, chlorine, or bromine.

The term "phenylalkyl" as used herein denotes phenyl attached to an alkyl as defined above. Examples include, but are not limited to, benzyl, phenethyl, and the like.

In the pictorial representation of the compounds given throughout this application, a thickened tapered line ( ▬ ) indicates a substituent which is above the plane of the ring to which the asymmetric carbon belongs and a dotted line ( ⋯ ) indicates a substituent which is below the plane of the ring to which the asymmetric carbon belongs.

Compounds of present invention can exhibit stereoisomerism. These compounds can be any isomer of the compound of Formula I, II, or III or mixtures of these isomers, including epimers. $R_P$ and $S_P$ as used herein refers to the stereochemistry at the phosphoros atom. The compounds and intermediates of the present invention having one or more asymmetric carbon atoms may be obtained as racemic mixtures of stereoisomers which can be resolved.

Compounds of Formula I, II, or III can exhibit tautomerism which means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of Formula I, II, or III which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

EMBODIMENTS

Method for Treatment of HCV

The application provides a method of treatment of HCV comprising administering to a patient in need thereof a combination of a compound of Formula I and a compound of Formula II:

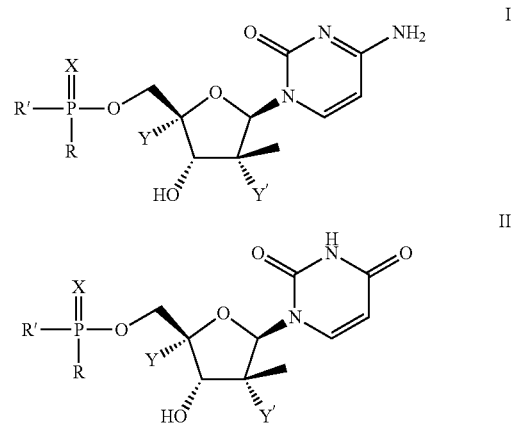

wherein:
each R is independently O—R$^1$ or NHC(R$^{2a}$)(R$^{2b}$)C(=O)OR$^3$;
each R' is independently O—R$^1$ or NHC(R$^{2a}$)(R$^{2b}$)C(=O)OR$^3$;
each R$^1$ is independently phenyl or naphthyl, optionally substituted with one or more lower alkyl, lower alkoxy, halo, lower haloalkyl, or cyano;
each R$^{2a}$ and R$^{2b}$ are independently H or lower alkyl;
each R$^3$ is independently H, lower alkyl, lower haloalkyl, cycloalkyl, phenyl or phenyl lower alkyl;
each X is independently O or S;
each Y is independently H or F; and
each Y' is independently F or OH;
or a pharmacologically acceptable salt thereof.

In one embodiment, the compound of Formula (I) is where each $R^3$ is independently H, lower alkyl, lower haloalkyl, phenyl or phenyl lower alkyl.

The application provides a method of treatment of HCV comprising administering to a patient in need thereof a combination of a compound of Formula I and a compound of Formula II wherein the compound of Formula I is:

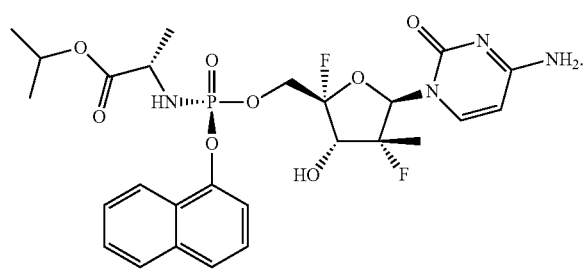 [SMILES: CC(C)OC(=O)[C@H](C)N[P@](=O)(OC[C@@]1(F)O[C@@H](n2ccc(N)nc2=O)[C@](C)(F)[C@@H]1O)Oc1cccc2ccccc12]

The application provides a method of treatment of HCV comprising administering to a patient in need thereof a combination of a compound of Formula I and a compound of Formula II wherein the compound of Formula I is:

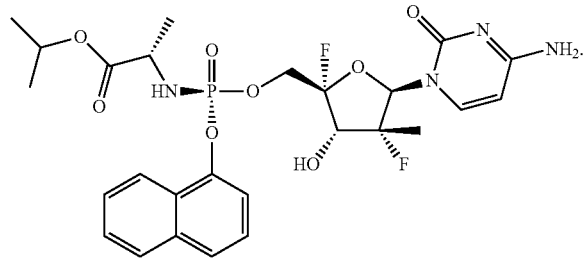 [SMILES: CC(C)OC(=O)[C@H](C)N[P@@](=O)(OC[C@@]1(F)O[C@@H](n2ccc(N)nc2=O)[C@](C)(F)[C@@H]1O)Oc1cccc2ccccc12]

The application provides a method of treatment of HCV comprising administering to a patient in need thereof a combination of a compound of Formula I and a compound of Formula II wherein the compound of Formula I is:

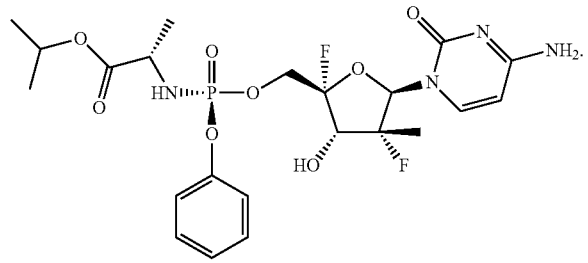 [SMILES: CC(C)OC(=O)[C@H](C)N[P@](=O)(OC[C@@]1(F)O[C@@H](n2ccc(N)nc2=O)[C@](C)(F)[C@@H]1O)Oc1ccccc1]

The application provides a method of treatment of HCV comprising administering to a patient in need thereof a combination of a compound of Formula I and a compound of Formula II wherein the compound of Formula I is:

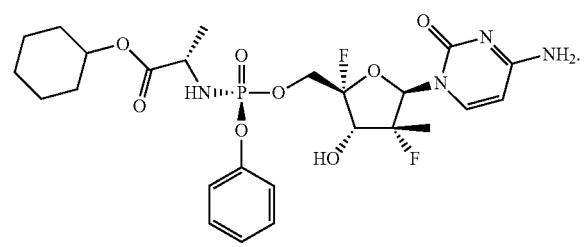 [SMILES: C[C@H](N[P@](=O)(OC[C@@]1(F)O[C@@H](n2ccc(N)nc2=O)[C@](C)(F)[C@@H]1O)Oc1ccccc1)C(=O)OC1CCCCC1]

The application provides a method of treatment of HCV comprising administering to a patient in need thereof a combination of a compound of Formula I and a compound of Formula II wherein the compound of Formula I is:

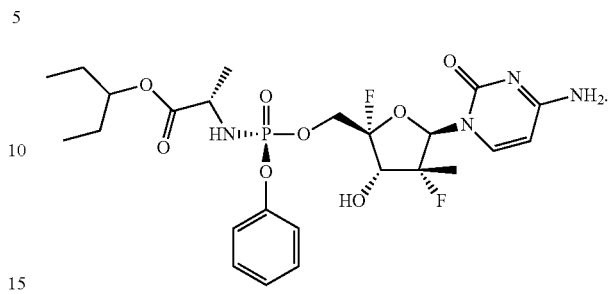

The application provides a method of treatment of HCV comprising administering to a patient in need thereof a combination of a compound of Formula I and a compound of Formula II wherein the compound of Formula I is:

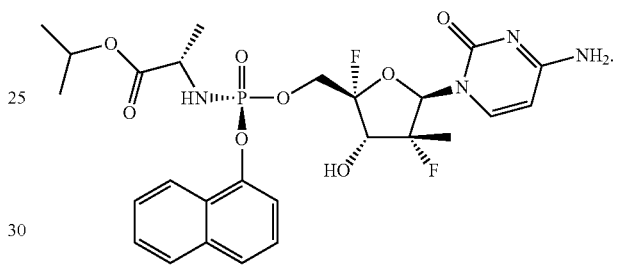

The application provides a method of treatment of HCV comprising administering to a patient in need thereof a combination of a compound of Formula I and a compound of Formula II wherein the compound of Formula I is:

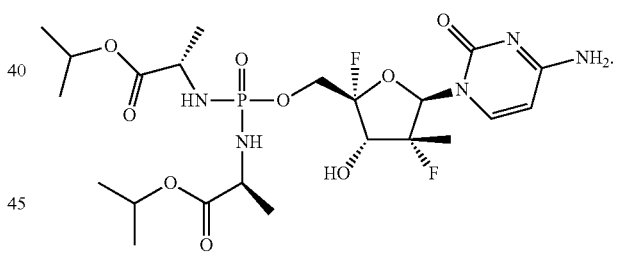

The application provides a method of treatment of HCV comprising administering to a patient in need thereof a combination of a compound of Formula I and a compound of Formula II wherein the compound of Formula I is:

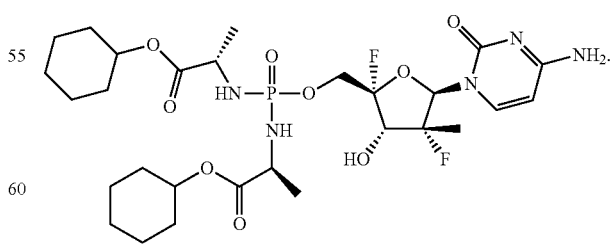

The application provides a method of treatment of HCV comprising administering to a patient in need thereof a combination of a compound of Formula I and a compound of Formula II wherein the compound of Formula I is:

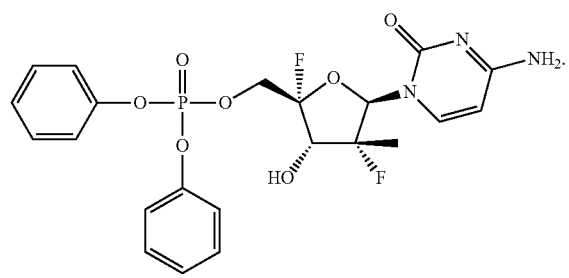

The application provides a method of treatment of HCV comprising administering to a patient in need thereof a combination of a compound of Formula I and a compound of Formula II wherein the compound of Formula I is:

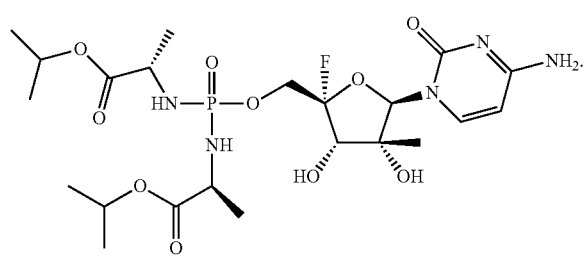 [SMILES: CC(C)OC(=O)[C@H](C)NP(=O)(N[C@@H](C)C(=O)OC(C)C)OC[C@@]1(F)O[C@@H](n2ccc(N)nc2=O)[C@](C)(F)[C@@H]1O]

The application provides a method of treatment of HCV comprising administering to a patient in need thereof a combination of a compound of Formula I and a compound of Formula II wherein the compound of Formula I is:

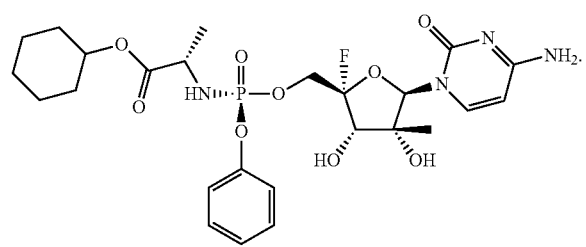 [SMILES: C[C@H](N[P@](=O)(OC[C@@]1(F)O[C@@H](n2ccc(N)nc2=O)[C@](C)(O)[C@@H]1O)Oc1ccccc1)C(=O)OC1CCCCC1]

The application provides a method of treatment of HCV comprising administering to a patient in need thereof a combination of a compound of Formula I and a compound of Formula II wherein the compound of Formula I is:

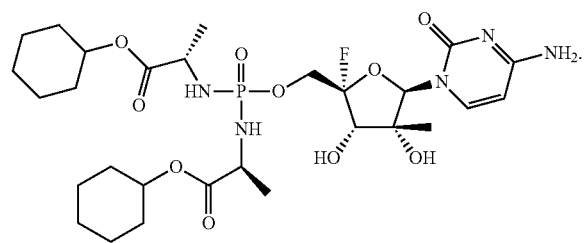 [SMILES: C[C@H](NP(=O)(N[C@@H](C)C(=O)OC1CCCCC1)OC[C@@]1(F)O[C@@H](n2ccc(N)nc2=O)[C@](C)(O)[C@@H]1O)C(=O)OC1CCCCC1]

The application provides a method of treatment of HCV comprising administering to a patient in need thereof a combination of a compound of Formula I and a compound of Formula II wherein the compound of Formula I is:

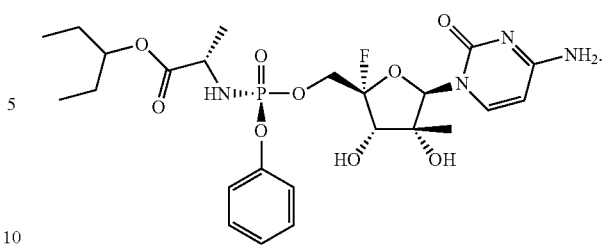

The application provides a method of treatment of HCV comprising administering to a patient in need thereof a combination of a compound of Formula I and a compound of Formula II wherein the compound of Formula I is:

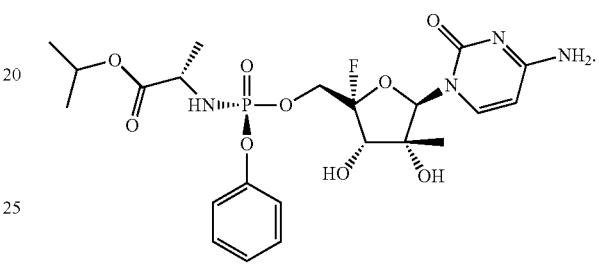

The application provides a method of treatment of HCV comprising administering to a patient in need thereof a combination of a compound of Formula I and a compound of Formula II wherein the compound of Formula I is:

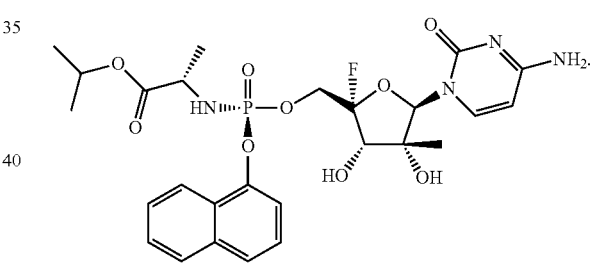

The application provides a method of treatment of HCV comprising administering to a patient in need thereof a combination of a compound of Formula I and a compound of Formula II wherein the compound of Formula I is:

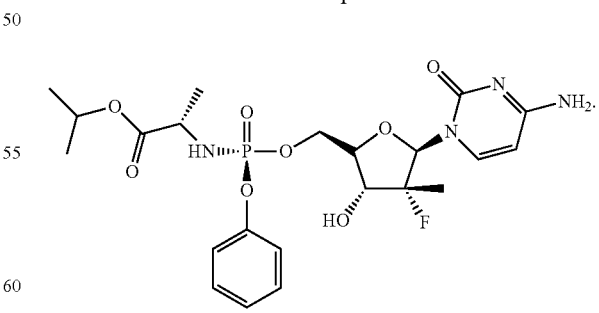

The application provides a method of treatment of HCV comprising administering to a patient in need thereof a combination of a compound of Formula I and a compound of Formula II wherein the compound of Formula II is Sofosbuvir:

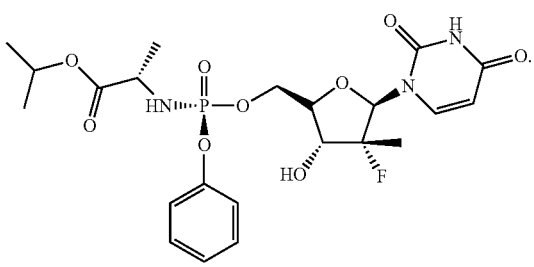

The application provides a method of treatment of HCV comprising administering to a patient in need thereof a combination of a compound of Formula I and a compound of Formula II wherein Formula II is:

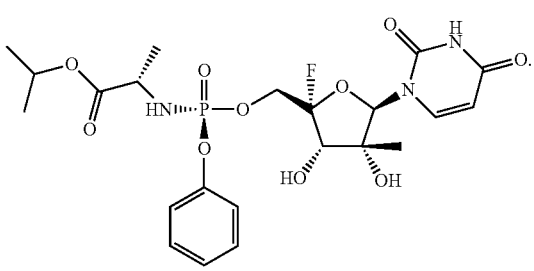

The application provides a method of treatment of HCV comprising administering to a patient in need thereof a combination of a compound of Formula I and a compound of Formula II wherein compound of Formula II is:

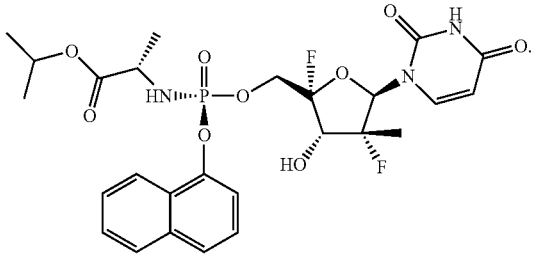

The application provides a method of treatment of HCV comprising administering to a patient in need thereof a combination of a compound of Formula I and a compound of Formula II wherein compound of Formula II is:

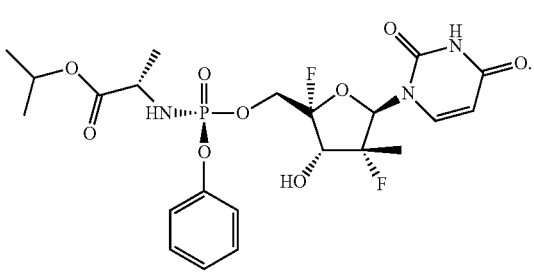

The application provides a method of treatment of HCV comprising administering to a patient in need thereof a combination of a compound of Formula I and a compound of Formula II wherein the compound of Formula I and the compound of Formula II are, respectively,

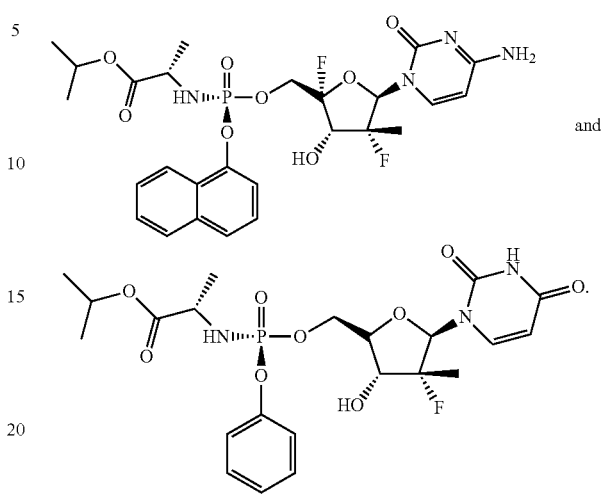

The application provides a method of treatment of HCV comprising administering to a patient in need thereof a combination of a compound of Formula I in and a compound of Formula II wherein the compound of Formula I and the compound of Formula II are, respectively,

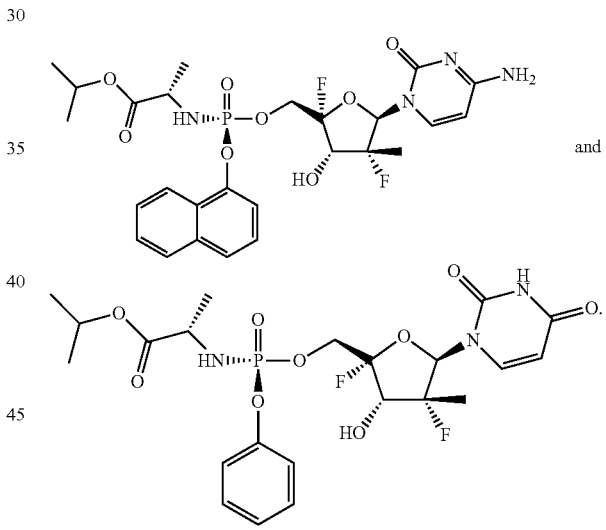

The application provides a method of treatment of HCV comprising administering to a patient in need thereof a combination of a compound of Formula I in and a compound of Formula II wherein the compound of Formula I and the compound of Formula II are, respectively,

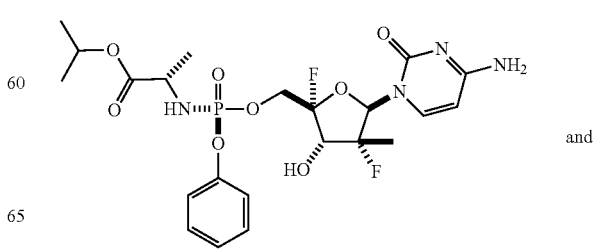

and

-continued

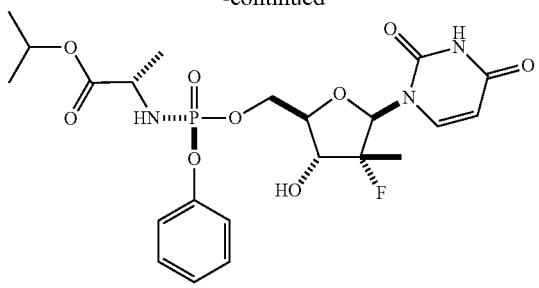

The application provides method of treatment of HCV comprising administering to a patient in need thereof a combination of a compound of Formula I in and a compound of Formula II wherein the compound of Formula I and the compound of Formula II are,

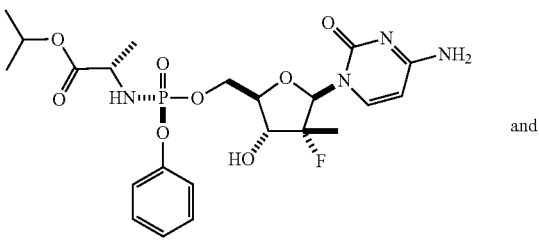

and

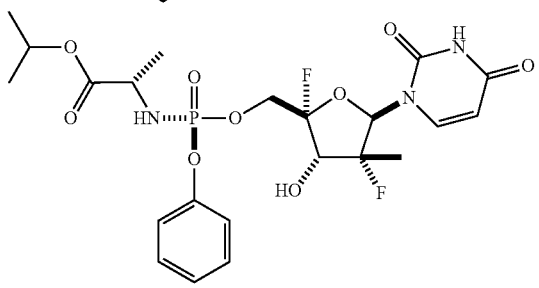

The application provides method of treatment of HCV comprising administering to a patient in need thereof a combination of a compound of Formula I in and a compound of Formula II wherein the compound of Formula I and the compound of Formula II are,

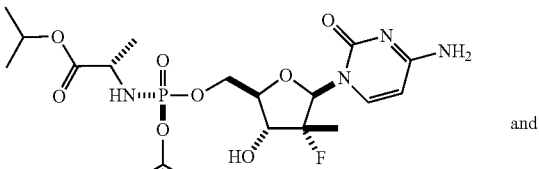

and

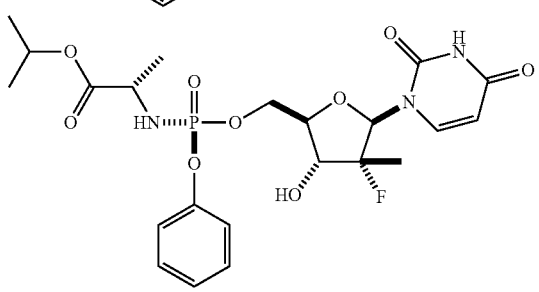

The application also provides a method of treatment of HCV comprising administering to a patient in need thereof a combination of a compound of Formula I and a compound of Formula II wherein the compound of Formula I is selected from the group consisting of:

isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

pentan-3-yl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

pentan-3-yl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate;

isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((S)-(((2S,3S,4R,5R)-5-(4-amino-2-oxopyrimidin-1(2H)-yl)-2-fluoro-3,4-dihydroxy-4-m ethyltetrahydrofuran-2-yl)methoxy)(naphthalen-1-yloxy)phosphoryl)-L-alaninate; and isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((S)-(((2S,3S,4R,5R)-5-(4-amino-2-oxopyrimi-din-1(2H)-yl)-2,4-difluoro-3-hydroxy-4-methyltetrahydrofuran-2-yl)methoxy)(naphthalen-1-yloxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

pentan-3-yl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

cyclohexyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

pentan-3-yl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate;

isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate; and isopropyl ((R)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate; and a mixture of $S_P$ and $R_P$ epimers thereof; or a pharmaceutically acceptable salt thereof of each of the foregoing compound.

In another embodiment, of preceding paragraph, compound of Formula (II) are independently selected from:

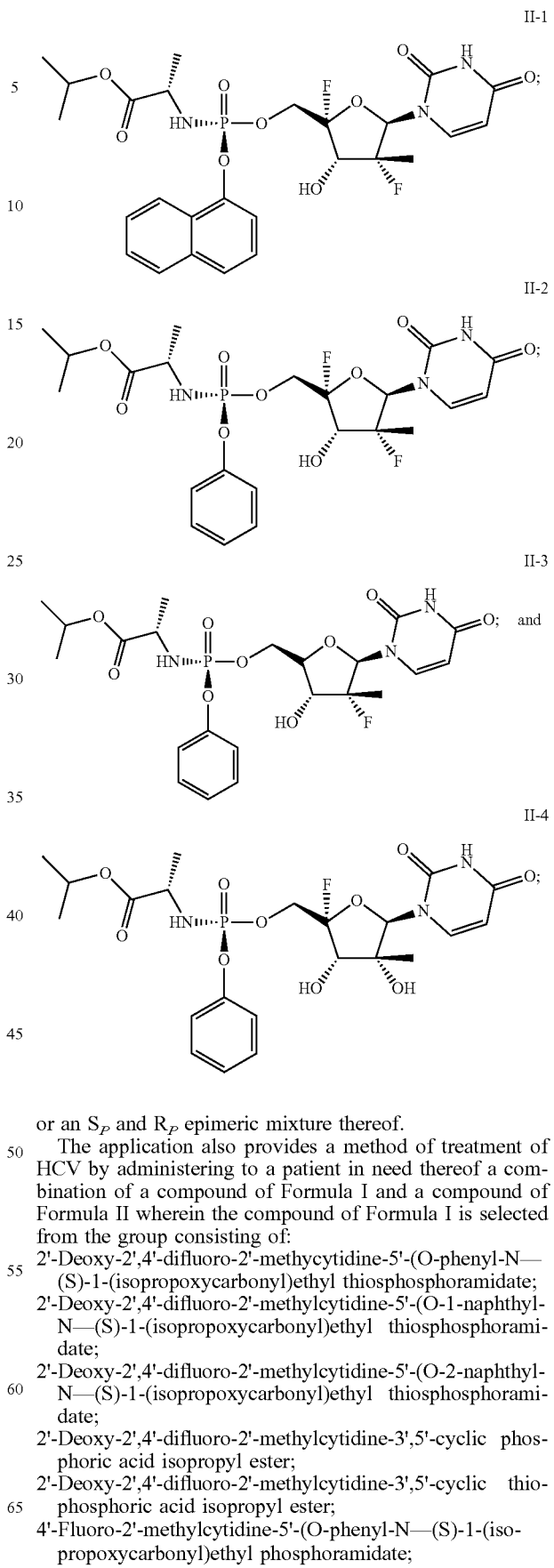

or an $S_P$ and $R_P$ epimeric mixture thereof.

The application also provides a method of treatment of HCV by administering to a patient in need thereof a combination of a compound of Formula I and a compound of Formula II wherein the compound of Formula I is selected from the group consisting of:

2'-Deoxy-2',4'-difluoro-2'-methycytidine-5'-(O-phenyl-N—(S)-1-(isopropoxycarbonyl)ethyl thiosphosphoramidate;

2'-Deoxy-2',4'-difluoro-2'-methylcytidine-5'-(O-1-naphthyl-N—(S)-1-(isopropoxycarbonyl)ethyl thiosphosphoramidate;

2'-Deoxy-2',4'-difluoro-2'-methylcytidine-5'-(O-2-naphthyl-N—(S)-1-(isopropoxycarbonyl)ethyl thiosphosphoramidate;

2'-Deoxy-2',4'-difluoro-2'-methylcytidine-3',5'-cyclic phosphoric acid isopropyl ester;

2'-Deoxy-2',4'-difluoro-2'-methylcytidine-3',5'-cyclic thiophosphoric acid isopropyl ester;

4'-Fluoro-2'-methylcytidine-5'-(O-phenyl-N—(S)-1-(isopropoxycarbonyl)ethyl phosphoramidate;

4'-Fluoro-2'-cytidine-5'-(O-1-naphthyl-N—(S)-1-(iso-propoxycarbonyl)ethyl phosphoramidate;
4'-Fluoro-2'-methylcytidine-5'-(O-1-naphthyl-N—(S)-2-(isopropoxycarbonyl)ethyl phosphoramidate;
4'-Fluoro-2'-methylcytidine-5'-(O-phenyl-N—(S)-1-(isopropoxycarbonyl)ethyl thiophsphoramidate;
4'-Fluoro-2'-methylcytidine-5'-(O-1-naphthyl-N—(S)-1-(isopropoxycarbonyl)ethyl thiophosphoramidate;
4'-Fluoro-2'-methylcytidine-5'-(O-1-naphthyl-N—(S)-2-(isopropoxycarbonyl)ethyl thiophosphoramidate;
4'-Fluoro-2'-methylcytidine-3',5'-cyclic phosphoric acid isopropyl ester;
4'-Fluoro-2'-methylcytidine-3',5'-cyclic thiophosphoric acid isopropyl ester;
2'-Deoxy-2',4'-difluoro-2'-methylcytidine-5'-{N,N'-bis[(S)-1-(isopropoxylcarbonyl)ethyl]-phosphorodiamidate;
2'-Deoxy-2',4'-difluoro-2'-methylcytidine-5'-{N,N'-bis[(S)-1-(isopropoxylcarbonyl)ethyl]-thiophosphorodiamidate;
4'-Fluoro-2'-methylcytidine-5'-{N,N'-bis[(S)-1-(isopropoxylcarbonyl)ethyl]-phosphorodiamidate; and
4'-Fluoro-2'-methylcytidine-5'-{N,N'-bis[(S)-1-(isopropoxylcarbonyl)ethyl]thiophosphorodiamidate.

The application also provides a method of treatment of HCV by administering to a patient in need thereof a combination of a compound of Formula I and a compound of Formula II wherein the compound of Formula II is selected from the group consisting of:
2'-Deoxy-2',4'-difluoro-2'-methyluridine-5'-(O-phenyl-N—(S)-1-(isopropoxycarbonyl)ethyl thiophosphoramidate;
2'-Deoxy-2',4'-difluoro-2'-methyluridine-5'-(O-2-naphthyl-N—(S)-1-(isopropoxycarbonyl)ethyl thiosphosphoramidate;
2'-Deoxy-2',4'-difluoro-2'-methyluridine-5'-(O-1-naphthyl-N—(S)-1-(isopropoxycarbonyl)ethyl thiophosphoramidate
2'-Deoxy-2',4'-difluoro-2'-methyluridine-3',5'-cyclic phosphoric acid isopropyl ester;
4'-Fluoro-2'-methyluridine-5'-(O-phenyl-N—(S)-1-(isopropoxycarbonyl)ethyl phosphoramidate;
4'-Fluoro-2'-methyluridine-5'-(O-1-naphthyl-N—(S)-1-(isopropoxycarbonyl)ethyl phosphoramidate;
4'-Fluoro-2'-methyluridine-5'-(O-1-naphthyl-N—(S)-2-(isopropoxycarbonyl)ethyl phosphoramidate;
4'-Fluoro-2'-methyluridine-5'-(O-phenyl-N—(S)-1-(isopropoxycarbonyl)ethyl thiophosphoramidate;
4'-Fluoro-2'-methyluridine-5'-(O-1-naphthyl-N—(S)-1-(isopropoxycarbonyl)ethyl thiophosphoramidate;
4'-Fluoro-2'-methyluridine-5'-(O-1-naphthyl-N—(S)-2-(isopropoxycarbonyl)ethyl thiophosphoramidate;
4'-Fluoro-2'-methyluridine-3',5'-cyclic phosphoric acid isopropyl ester;
4'-Fluoro-2'-methyluridine-3',5'-cyclic thiophosphoric acid isopropyl ester;
2'-Deoxy-2',4'-difluoro-2'-methyluridine-5'-{N,N'-bis[(S)-1-(isopropoxylcarbonyl)ethyl]-phosphorodiamidate;
2'-Deoxy-2',4'-difluoro-2'-methyluridine-5'-{N,N'-bis[(S)-1-(isopropoxylcarbonyl)ethyl]-thiophosphorodiamidate;
4'-Fluoro-2'-methyluridine-5'-{N,N'-bis[(5)-1-(isopropoxylcarbonyl)ethyl]phosphorodiamidate; and
4'-Fluoro-2'-methyluridine-5'-{N,N'-bis[(5)-1-(isopropoxylcarbonyl)ethyl]-thiophosphorodiamidate.

Also provided are methods of treatment of HCV comprising administering to a patient in need thereof a combination of a compound of Formula I and a compound of Formula II (or any of the embodiments thereof herein), the method further comprising administering one or more of ribavirin, peginterferon-α, simeprevir, ledipasvir, daclatasvir, and velpatasvir.

The application also provides a method of treatment of HCV comprising administering to a patient in need thereof, a composition comprising a compound of Formula I and/or a compound of Formula II

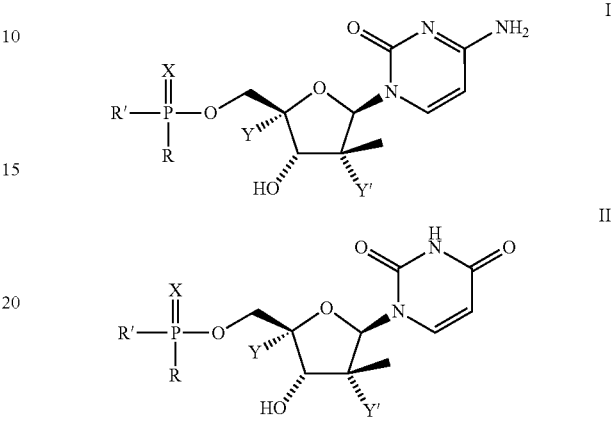

wherein:
each R is independently O—R₁ or NHC(R$^{2a}$)(R$^{2b}$)C(=O)OR³;
each R' is independently O—R¹ or NHC(R$^{2a}$)(R$^{2b}$)C(=O)OR³;
each R¹ is independently phenyl or naphthyl, optionally substituted with one or more lower alkyl, lower alkoxy, halo, lower haloalkyl, or cyano;
each R$^{2a}$ and R$^{2b}$ are independently H or lower alkyl;
each R³ is independently H, lower alkyl, lower haloalkyl, cycloalkyl, phenyl or phenyl lower alkyl;
each X is independently O or S;
each Y is independently H or F; and
each Y' is independently F or OH;
or a pharmacologically acceptable salt thereof;
(or any embodiments thereof herein) admixed with at least one carrier, diluent or excipient.

The application additionally provides a method of treatment of HCV comprising administering to a patient in need thereof a compound of Formula I, or a combination of Formula I and Formula II:

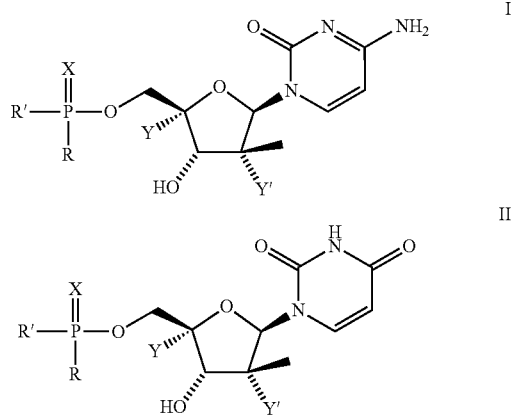

wherein:
each R is independently O—R¹ or NHC(R$^{2a}$)(R$^{2b}$)C(=O)OR³;

each R' is independently O—R¹ or NHC($R^{2a}$)($R^{2b}$)C(=O)OR³;
  each R¹ is independently phenyl or naphthyl, optionally substituted with one or more lower alkyl, lower alkoxy, halo, lower haloalkyl, or cyano;
  each $R^{2a}$ and $R^{2b}$ are independently H or lower alkyl;
  each R³ is independently H, lower alkyl, lower haloalkyl, cycloalkyl, phenyl or phenyl lower alkyl;
  each X is independently O or S;
  each Y is independently H or F; and
  each Y' is independently F or OH;
or a pharmacologically acceptable salt thereof;
(or an embodiment thereof herein), further in combination with a NS3A HCV protease inhibitor.

The application further provides a method of treatment of HCV comprising administering to a patient in need thereof a compound of Formula I, or a combination of Formula I and Formula II:

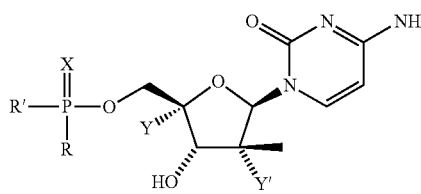

I

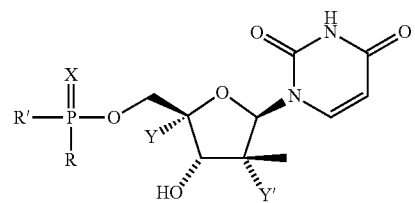

II wherein:
  each R is independently O—R¹ or NHC($R^{2a}$)($R^{2b}$)C(=O)OR³;
  each R' is independently O—R¹ or NHC($R^{2a}$)($R^{2b}$)C(=O)OR³;
  each R¹ is independently phenyl or naphthyl, optionally substituted with one or more lower alkyl, lower alkoxy, halo, lower haloalkyl, or cyano;
  each $R^{2a}$ and $R^{2b}$ are independently H or lower alkyl;
  each R³ is independently H, lower alkyl, lower haloalkyl, cycloalkyl, phenyl or phenyl lower alkyl;
  each X is independently O or S;
  each Y is independently H or F; and
  each Y' is independently F or OH;
or a pharmacologically acceptable salt thereof;
(or any embodiment thereof herein) further in combination with an additional NS5B HCV polymerase inhibitor.

The application provides a method for inhibiting replication of HCV in a cell comprising administering a combination of a compound of Formula I and/or a compound of Formula II.

The application provides a use of a combination of the compound of Formula I and the compound of Formula II in the manufacture of a medicament for the treatment of HCV.

The application provides a compound, composition, or method as described herein.

Examples of representative compounds of Formula (I) encompassed by the present invention and within the scope of the invention are provided in Table 1 below.

In general, the nomenclature used in this Application is based on standard nucleic acid nomenclature common to one of ordinary skill in the art. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| Compound Number | Structure | Name |
|---|---|---|
| I-1 | 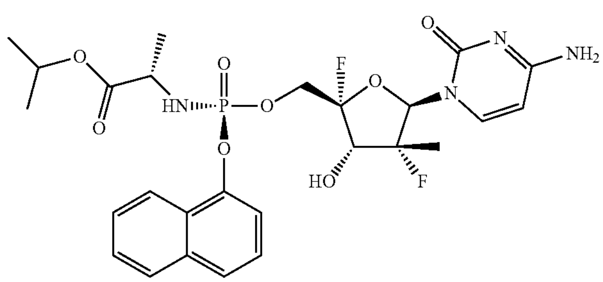 [SMILES: CC(C)OC(=O)[C@H](C)N[P@](=O)(OC[C@@]1(F)O[C@@H](n2ccc(N)nc2=O)[C@](C)(F)[C@@H]1O)Oc1cccc2ccccc12] | isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate |
| I-2 | 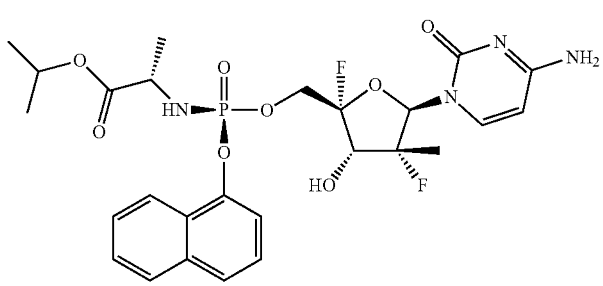 [SMILES: CC(C)OC(=O)[C@H](C)N[P@](=O)(OC[C@@]1(F)O[C@@H](n2ccc(N)nc2=O)[C@](C)(F)[C@@H]1O)Oc1cccc2ccccc12] | isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate |

TABLE 1-continued

| Compound Number | Structure | Name |
|---|---|---|
| I-3 | 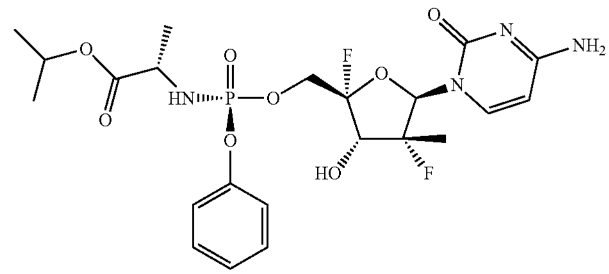 [SMILES: CC(C)OC(=O)[C@H](C)N[P@](=O)(OC[C@@]1(F)O[C@@H](n2ccc(N)nc2=O)[C@](C)(F)[C@@H]1O)Oc1ccccc1] | isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-4 | 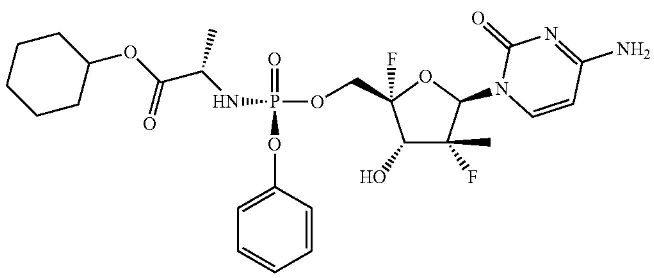 [SMILES: C[C@H](N[P@](=O)(OC[C@@]1(F)O[C@@H](n2ccc(N)nc2=O)[C@](C)(F)[C@@H]1O)Oc1ccccc1)C(=O)OC1CCCCC1] | cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-5 | 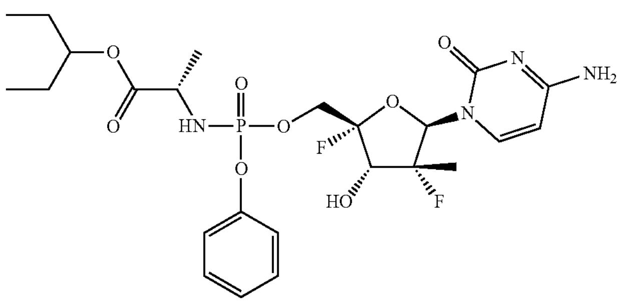 [SMILES: CCC(CC)OC(=O)[C@H](C)NP(=O)(OC[C@@]1(F)O[C@@H](n2ccc(N)nc2=O)[C@](C)(F)[C@@H]1O)Oc1ccccc1] | pentan-3-yl-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-6 | 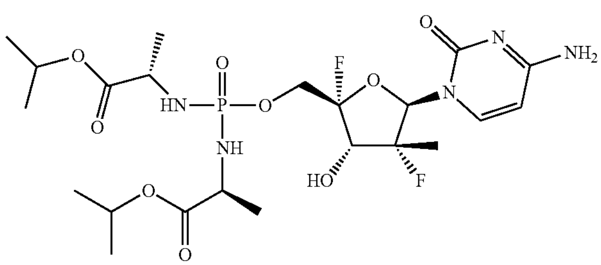 [SMILES: CC(C)OC(=O)[C@H](C)NP(=O)(N[C@@H](C)C(=O)OC(C)C)OC[C@@]1(F)O[C@@H](n2ccc(N)nc2=O)[C@](C)(F)[C@@H]1O] | diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate |
| I-7 | 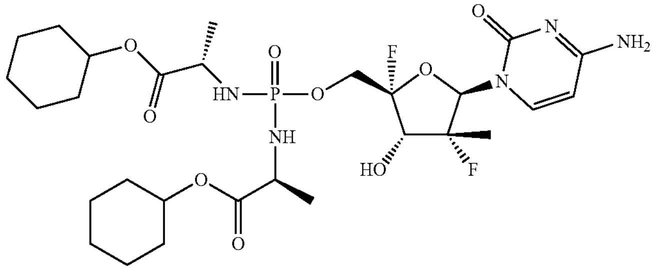 [SMILES: C[C@H](NP(=O)(N[C@@H](C)C(=O)OC1CCCCC1)OC[C@@]1(F)O[C@@H](n2ccc(N)nc2=O)[C@](C)(F)[C@@H]1O)C(=O)OC1CCCCC1] | dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate |

TABLE 1-continued

| Compound Number | Structure | Name |
|---|---|---|
| I-8 | 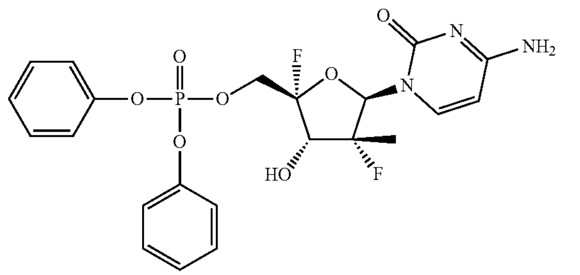 [SMILES: C[C@]1(F)[C@H](n2ccc(N)nc2=O)O[C@](F)(COP(=O)(Oc2ccccc2)Oc2ccccc2)[C@H]1O] | ((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate |
| I-9 | 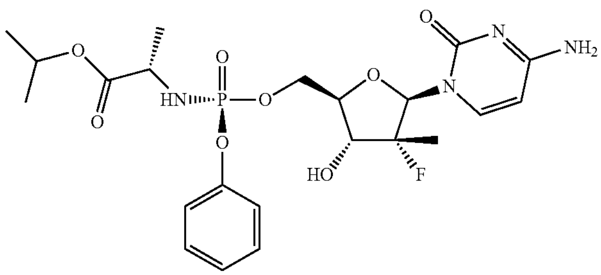 [SMILES: CC(C)OC(=O)[C@H](C)N[P@](=O)(OC[C@H]1O[C@@H](n2ccc(N)nc2=O)[C@](C)(F)[C@@H]1O)Oc1ccccc1] | isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate |
| I-10 | 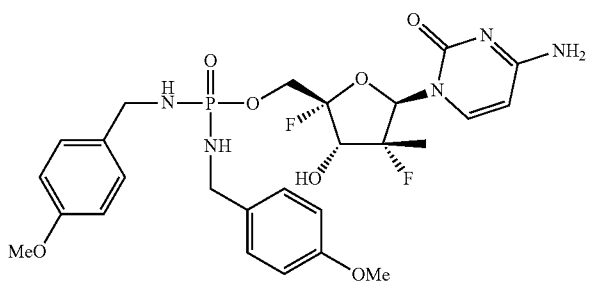 [SMILES: COc1ccc(CNP(=O)(NCc2ccc(OC)cc2)OC[C@@]2(F)O[C@@H](n3ccc(N)nc3=O)[C@](C)(F)[C@@H]2O)cc1] | ((2S,3S,4R,5R)-5-(4-amino-2-oxopyrimidin-1(2H)-yl)-2,4-difluoro-3-hydroxy-4-methyltetrahydrofuran-2-yl)methyl bis(4-methoxybenzyl)phosphordiamidate |

Additional compounds of Formula I that can be used in the methods disclosed herein are disclosed in Table 2 below:

TABLE 2

| Compound Number | Structure | Name |
|---|---|---|
| I-11 | 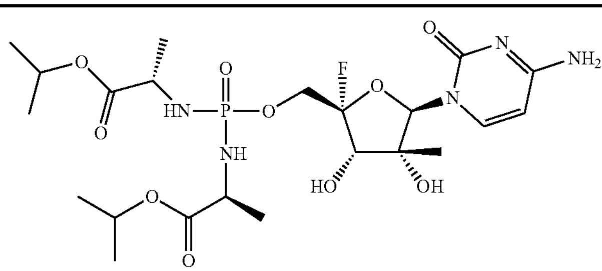 | diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate |
| I-12 | 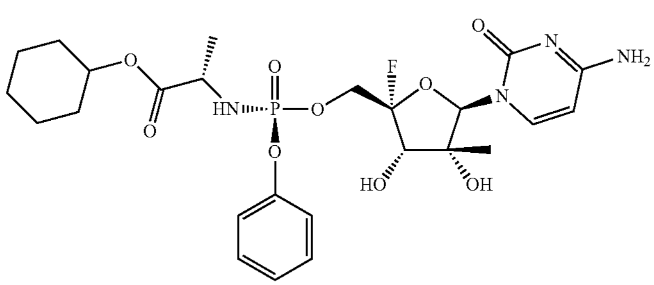 [SMILES: C[C@H](N[P@](=O)(OC[C@@]1(F)O[C@@H](n2ccc(N)nc2=O)[C@](C)(O)[C@@H]1O)Oc1ccccc1)C(=O)OC1CCCCC1] | cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate |

TABLE 2-continued

| Compound Number | Structure | Name |
|---|---|---|
| I-13 | 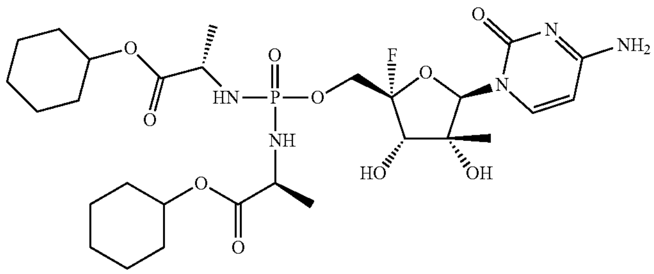 [SMILES: C[C@H](NP(=O)(N[C@@H](C)C(=O)OC1CCCCC1)OC[C@@]1(F)O[C@@H](n2ccc(N)nc2=O)[C@](C)(O)[C@@H]1O)C(=O)OC1CCCCC1] | dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate |
| I-14 | 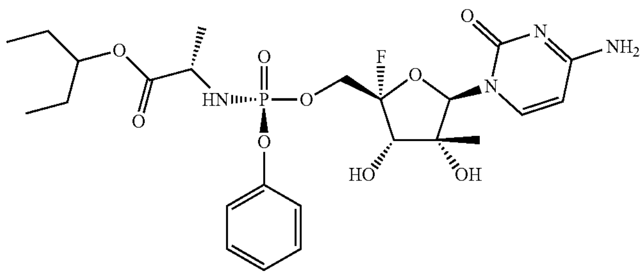 [SMILES: CCC(CC)OC(=O)[C@H](C)N[P@](=O)(OC[C@@]1(F)O[C@@H](n2ccc(N)nc2=O)[C@](C)(O)[C@@H]1O)Oc1ccccc1] | pentan-3-yl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate |
| I-15 | 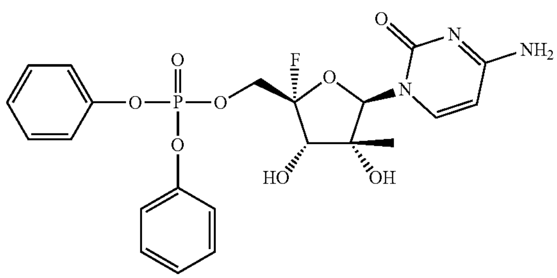 [SMILES: C[C@]1(O)[C@H](n2ccc(N)nc2=O)O[C@](F)(COP(=O)(Oc2ccccc2)Oc2ccccc2)[C@H]1O] | ((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate |
| I-16 | 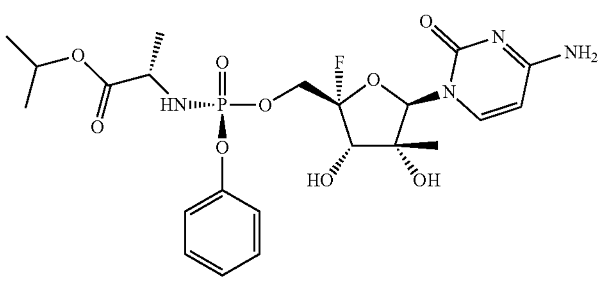 [SMILES: CC(C)OC(=O)[C@H](C)N[P@](=O)(OC[C@@]1(F)O[C@@H](n2ccc(N)nc2=O)[C@](C)(O)[C@@H]1O)Oc1ccccc1] | isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate |
| I-17 | 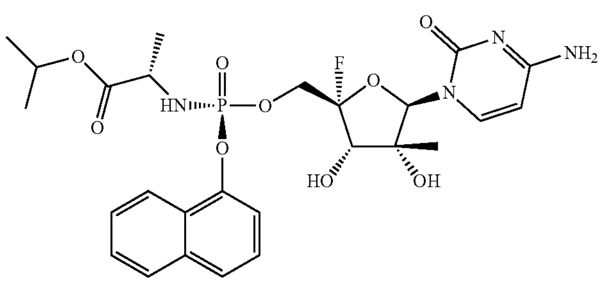 [SMILES: CC(C)OC(=O)[C@H](C)N[P@](=O)(OC[C@@]1(F)O[C@@H](n2ccc(N)nc2=O)[C@](C)(O)[C@@H]1O)Oc1cccc2ccccc12] | isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate |

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, DX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/4038 1; WO00/56331, WO02/04425; WO03/007945; WO03/010141; WO03/000254; WO01/32153; WO000/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a hepatitis C virus (HCV) infection comprising administering to a patient in need thereof a therapeutically effective amount of a compound of any one of compounds of the invention.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

It will be understood that references herein to treatment extend to prophylaxis as well as to the treatment of existing conditions, and that the treatment of animals includes the treatment of humans as well as other mammals. Furthermore, treatment of an hepatitis C virus (HCV) infection, as used herein, also includes treatment or prophylaxis of a disease or a condition associated with or mediated by hepatitis C virus (HCV) infection, or the clinical symptoms thereof.

Dosage and Administration

As shown in Biological Examples, Table A below, the compounds of Formula I have the potential to be efficacious as antiviral drugs for the treatment of HCV infections in humans, or are metabolized to a compound that exhibit such activity.

The active compound or its prodrug derivative or salt can be administered in combination with another antiviral agent, such as an anti-hepatitis agent, including those of Formula I. When the active compound or its derivative or salt are administered in combination with another antiviral agent the activity may be increased over the parent compound. This can easily be assessed by preparing the derivative and testing its anti-HCV activity according to the method described herein.

Administration of the active compound may range from continuous (intravenous drip) to several oral administrations per day (for example, Q.I.D) and may include oral, topical parenteral, intramuscular, intravenous, subcutaneous, transdermal (which may include a penetration enhancement agent), buccal and suppository administration, among other routes of administration.

The compounds disclosed herein as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatin capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the compound disclosed herein, as well as their pharmaceutically useable salts, can be formulated with a therapeutically inert, inorganic or organic excipient for the production of tablets, coated tablets, dragées, hard and soft gelatin capsules, solutions, emulsions or suspensions.

The compounds disclosed herein can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, drages, and hard gelatin capsules are, for example, lactose, corn starch and derivatives thereof, talc, and stearic acid or its salts. If desired, the tablets or capsules may be enteric-coated or sustained release by standard techniques. Suitable excipients for soft gelatin capsules are, for example, vegetable oils, waxes, fats, semi-solid and liquid polyols. Suitable excipients for injection solutions are, for example, water, saline, alcohols, polyols, glycerin or vegetable oils. Suitable excipients for suppositories are, for example, natural and hardened oils, waxes, fats, semi-liquid or liquid polyols. Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants. The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to targeted site within the host organism or patient to maximize the intended effect of the compound.

GENERAL SYNTHESIS

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Synthesis of compounds of Formula II

Compounds of Formula II can be prepared as illustrated and described in Schemes 1 to 4 below.

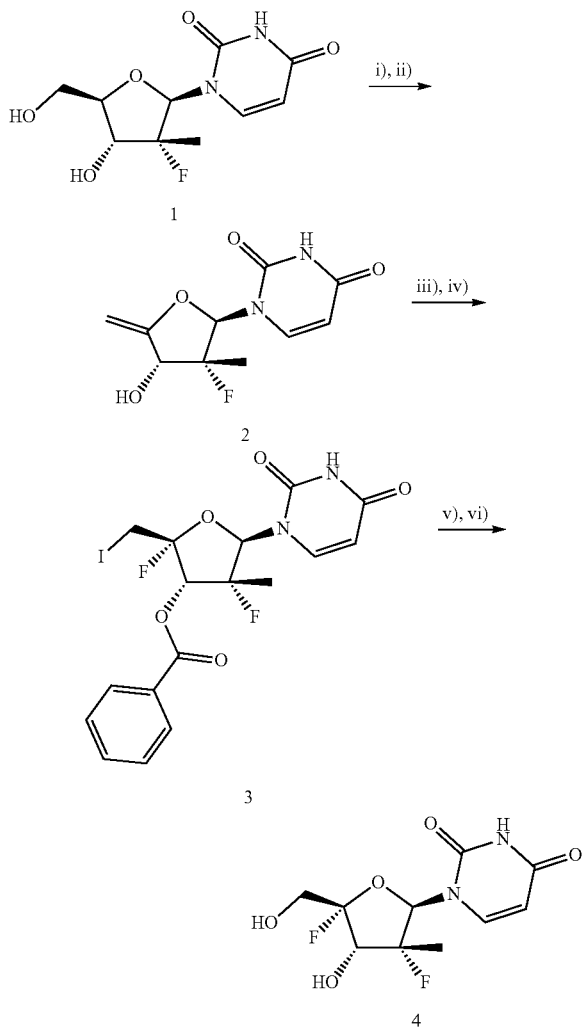

Scheme 1
Synthesis of 1-((2R,3R,4S,5S)-3,5-difluoro-4-hydroxy-5-(hydroxymethyl)-3-methyltetrahydrofuran-2-yl)pyrimidine-2,4(1H,3H)-dione i) I$_2$, PPh$_3$, THF; ii) NaOMe, MeOH; iii) BzCl, DMAP, THF; iv) I$_2$, AgF,CH$_2$Cl$_2$; v) PhCO$_2$Na, DMSO; vi) NH$_3$, MeOH The starting material 1 can be prepared according to the procedures described by Sofia, M. J. et al, *J. Med. Chem.*

(2010), 53(19),7202-7218 and Clark, J. L. et al, *J. Med. Chem.* (2005), 48(17),5504-5508. Iodination of 1 followed by elimination of iodide under basic condition can lead to intermediate 2. Protection of 3'-hydroxy in 2 with benzoyl group, followed by a key stereospecific fluorination reaction can give intermediate 3. Similar transformation to install a fluoride at 4' α position has been described previously by Ajmera, S. et al, *J. Med. Chem.* (1988), 31(6),1094-1098 and Moffatt, J. G. et al, *J. Am. Chem. Soc.* (1971), 93(17), 4323-4324. Displacement of 5' iodide in 3 with sodium benzoate followed by deprotection of 3', 5' benzoyl groups gives the nucleoside intermediate 4.

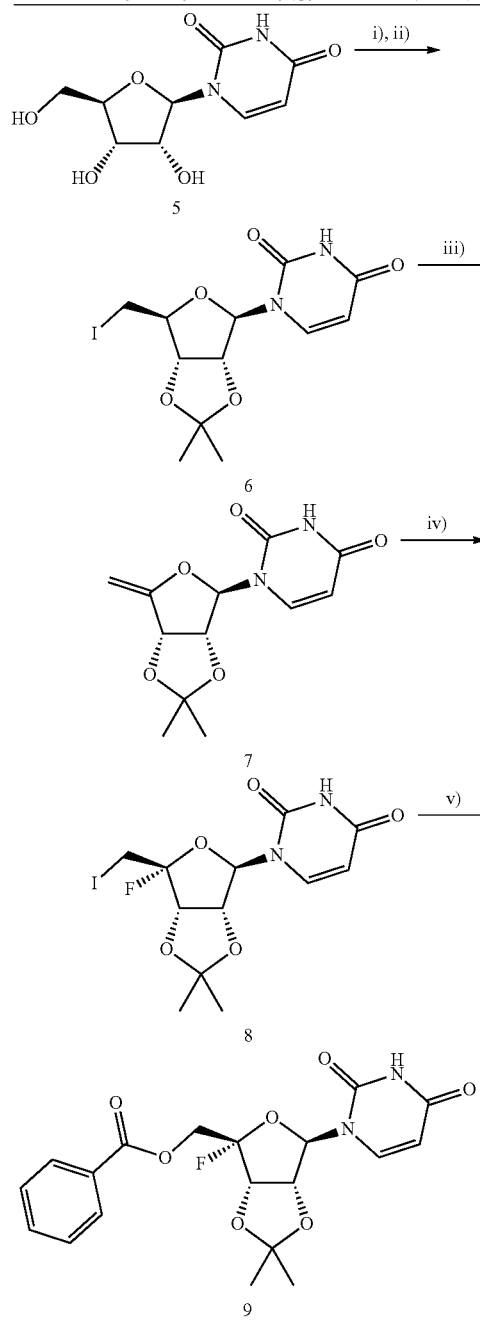

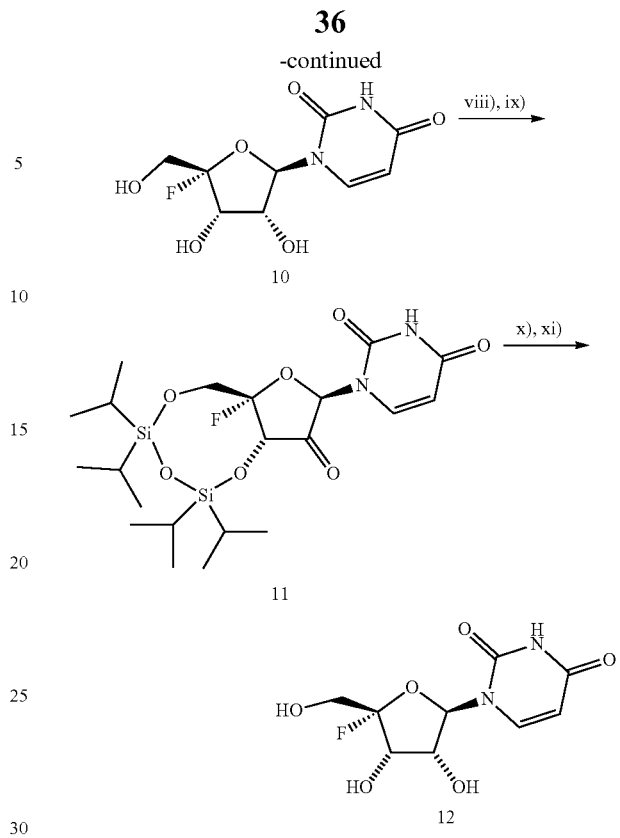

i) Acetone, PTSA; ii) I$_2$, PPh$_3$, THF; iii) NaOMe, MeOH; iv) I$_2$, AgF, CH$_2$Cl$_2$; v) PhCO$_2$Na, DMSO; vi) NH$_3$, MeOH; vii) Formic acid; viii) DIPSCl, Pyridine; ix) Dess-Martin, CH$_2$Cl$_2$; x) AlCl$_3$, CH$_2$Cl$_2$; xi) TBAF, THF.

Protection, iodination and then elimination of iodo under basic conditions provides intermediate 7. Fluorination of 7 at the 4'-position can be carried out as described in Ajmera, S. et al, *J. Med. Chem.* (1988), 31(6),1094-1098 and Moffatt, J. G. et al, *J. Am. Chem. Soc.* (1971), 93(17), 4323-4324. Displacement of 5' iodide 8 with sodium benzoate should afford intermediate 9. Deprotection followed by selective protection of the 3' and 5'-hydroxy group with 1,3-dichloro-1,1,3,3-tetraisopropyldisiloxane (DIPSCl) followed by oxidation under Dess-Martin conditions can give the ketone 11, following a similar method described by Hayakawa, H et al., *Chem. Pharm. Bull.*, (1987), 35(6), 2605-2608. Deprotection under standard conditions to remove a silyl protecting group should yield the desired product 12.

Scheme 3
Synthesis of a compound of Formula II where Base is uracil, X is O or S, R is —OAr where Ar is phenyl or naphthyl and R' is NHCH(CH$_3$)C(=O)O-isopropyl, Y is F and Y' is OH or F

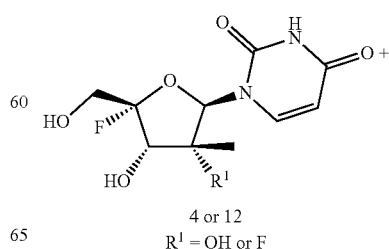

4 or 12
R$^1$ = OH or F

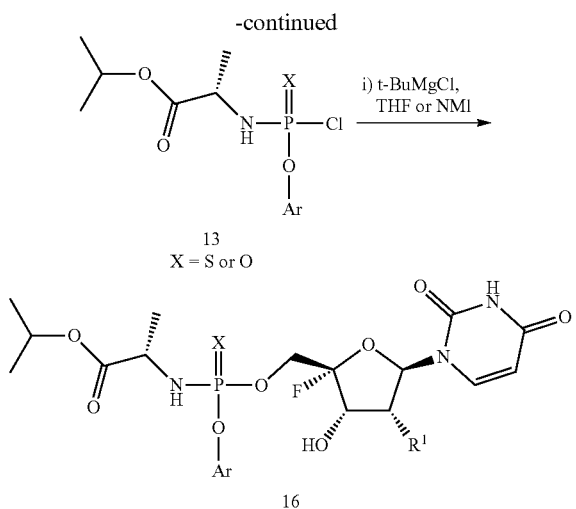

13
X = S or O

16

Phosphoramidate compounds of Formula II can be prepared by condensation of nucleoside 4 or 12 with a suitably substituted phosphochloridate, or its sulfur analogue, of type 13 in the presence of a strong base. The coupled product 16 of Formula II is obtained as a mixture of two diastereomers initially under the coupling reaction and can be separated into their corresponding chiral enantiomers by chiral column, chiral HPLC, or chiral SFC chromatography.

Scheme 4
Synthesis of a compound of Formula II where Base is uracil, X is O or S, R and R' are NHCH(CH₃)C(=O)O-isopropyl, Y is F and Y' is OH or F

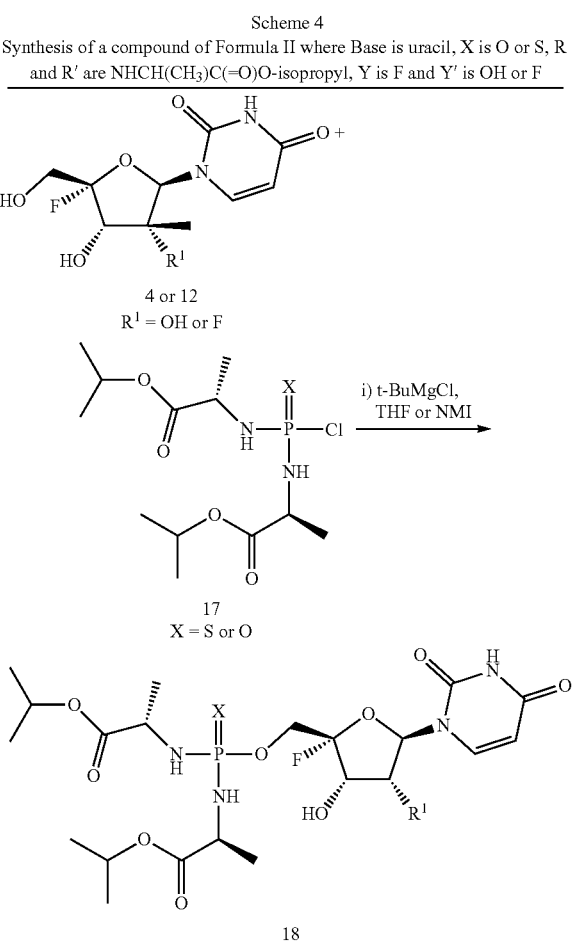

4 or 12
R¹ = OH or F

17
X = S or O

18

Phosphorodiamidate compounds of Formula II in the present invention can be prepared by condensation of nucleoside 4 or 12 with a suitably substituted phosphorodiamidic chloride, or phosphorodiamidothioic chloride, of type 17 in the presence of a strong base.

Compounds of Formula (I) can be prepared by methods disclosed in Schemes 1-4 above utilizing the methods known in the art and Examples below.

EXAMPLES

These examples and preparations which follow are provided to enable those skilled in the art to more clearly understand and to practice the present invention. They should not be considered as limiting the scope of the invention, but merely as being illustrative and representative thereof.

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzoyl (Bz), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-isopropylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-BuMe₂Si, (TBDMS), 4-N,N-dimethylaminopyridine (DMAP), triethylamine (Et₃N or TEA), N,N-dimethylformamide (DMF), triflate or $CF_3SO_2$—(Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et₂O), trimethylsilyl or Me₃Si (TMS), ethyl (Et), p-toluenesulfonic acid monohydrate (TsOH or pTsOH), lithium hexamethyl disilazane (LiHMDS), 4-Me-C₆H₄SO₂— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

SYNTHETIC EXAMPLES

The following preparations of compounds of Formula I and intermediates (References) are given to enable those skilled in the art to more clearly understand and to practice the present disclosure. They should not be considered as limiting the scope of the disclosure, but merely as being illustrative and representative thereof.

All reactions were carried out using commercial materials and reagents without further purification unless otherwise noted. All reactions were monitored by thin layer chromatography (TLC) on silica gel plates (Keiselgel 60 F254, Merck) and/or ultra-performance liquid chromatography (UPLC). Visualization of the spots on TLC plates was achieved by UV light and by staining the TLC plates in potassium permanganate and charring with a heat gun. UPLC 1 was recorded on a Waters Acquity UPLC instrument with Acquity PDA detector, QDA mass detector and binary solvent system. UPLC 2 was recorded on a Waters Acquity UPLC HClass instrument with Acquity PDA detector, QDA mass detector and quaternary solvent system. UPLC 1 acidic methods were run using varying gradients of 0.1% formic acid in acetonitrile and 0.1% formic acid in water on a CSH C18 column (2.1×50 mm 1.7 μm) at 0.8 mL/min. UPLC 2 acidic methods were run using varying gradients of acetonitrile, water and 2% formic acid in water on a CSH C18 column (2.1×50 mm 1.7 μm) at 0.8 mL/min. Basic methods were run using varying gradients of acetonitrile and 10 mM $NH_4HCO_3$ adjusted to pH 10 with ammonia solution in water on either a XB C18 column (2.1×50 mm 2.5 μm) or XB C8 column (2.1×50 mm 2.5 μm) at 0.8 mL/min. All products were characterized by $^1H$ NMR and where appropriate $^{13}C$, $^{31}P$ and $^{19}F$ NMR. NMR spectral data was recorded on a JEOL ECX300 MHz or JEOL ECX400 MHz spectrometer. Chemical shifts are expressed in parts per million values (ppm) and are designated as s (singlet); br s (broad singlet); d (doublet); t (triplet); q (quartet); quint (quintet) or m (multiplet). Flash column chromatography was performed on silica gel using Fluorochem silicagel LC60A 40-63 micron and reagent grade heptane, ethyl acetate, dichloromethane and methanol as eluent. Mass directed preparative HPLC was carried out using a Waters auto purification system with a PDA detector and 3100 mass detector with either an X-Bridge C18 column (19×150 mm) or XSelect C18 column (19×150 mm) at 20 mL/min.

Reference 1

Synthesis of 4-amino-1-((2R,3R,4 S,5 S)-3,5-difluoro-4-hydroxy-5-(hydroxymethyl)-3-methyltetrahydrofuran-2-yl)pyrimidin-2(1H)-one 25

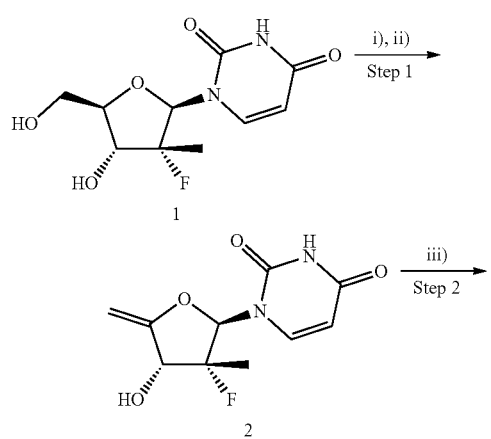

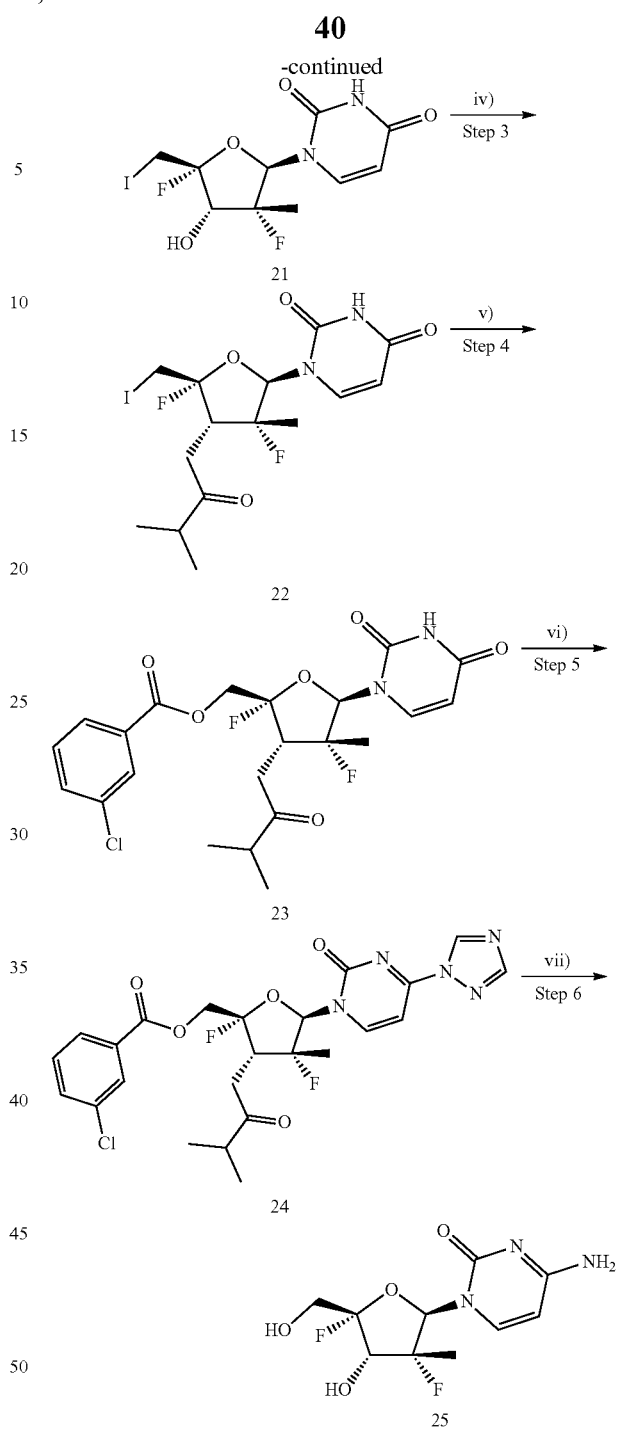

i) $PPh_3$, $I_2$, Imidazole, THF; ii) NaOMe, MeOH, 60° C.; iii) $Et_3N\cdot 3HF$, NIS, $CH_2Cl_2$; iv) iPrCOCl, DMAP, $Et_3N$, EtOAc; v) m-CPBA, $K_2HPO_4$, $Bu_4NHSO_4$, EtOAc, $H_2O$; vi) 1,2,4-triazole, $POCl_3$, $Et_3N$, $CH_2CL_2$; vii) $NH_4OH$, THF then $NH_3$/MeOH.

Step 1: Preparation of 1-[(2R,3R,4R)-3-fluoro-4-hydroxy-3-methyl-5-methylideneoxolan-2-yl]-1,2,3,4-tetrahydropyrimidine-2,4-dione 2

Step (i): To a stirred solution of 1-[(2R,3R,4R,5S)-3-fluoro-4-hydroxy-3-methyloxolan-2-yl]-1,2,3,4-tetrahydropyrimidine-2,4-dione 1 (2602 g, 10.00 mol, 1 eq), $PPh_3$ (3410 g, 13.00 mol, 1.30 eq) and imidazole (885.0 g, 13.00 mol, 1.30 eq) in THF (25 L) was added iodine (2665 g, 10.50 mol, 1.05 eq) in portions during a period of 1 h while keeping inner temperature between 10° C.-20° C. The stirred reaction mixture was allowed to warm to ambient temperature for 20 h. The suspension was filtered and the filtrate was concentrated to give the crude product as a light yellow oil. The residue was suspended in methanol (8.0 L), the solid was collected and washed with petroleum ether (8 L), dried to give 3430 g of 1-[(2R,3R,4R,5S)-3-fluoro-4-hydroxy-5-(iodomethyl)-3-methyloxolan-2-yl]-1,2,3,4-tetrahydropyrimidine-2,4-dione (92.67%) as a white solid. $^1$H NMR (DMSO-d6,400 MHz) $\delta_H$ 11.52 (s, 1H), 7.61-7.63 (d, 1H), 5.91-6.05 (m, 2H), 5.675.69 (d, J=20 HZ, 1H), 4.06-4.10 (m, 1H), 3.77-3.80 (m, 1H), 3.49-3.65 (m, 3H), 1.21-1.27 (d, 3H).

Step (ii): To a solution of 1-[(2R,3R,4R,5S)-3-fluoro-4-hydroxy-5-(iodomethyl)-3-methyloxolan-2-yl]-1,2,3,4-tetrahydropyrimidine-2,4-dione (5000 g, 13.509 mol, 1.0 eq) in methanol (25.0 L) was added sodium methoxide (30% in methanol, 6080 g, 33.77 mol, 2.5 eq). The reaction mixture was stirred at 60° C. for 5 h and then cooled to 10° C. The suspension was filtered and the filtrate was concentrated to give the crude product as a brown yellow solid which was used directly in the next step without further purification.

The crude residue was dissolved in acetonitrile (25.0 L) and acetic anhydride (2758 g, 27.018 mol, 2.00 eq) was added. The reaction mixture was stirred at 65° C. for 15 h. Based on LC-MS, an additional amount of the acetic anhydride (276.0 g, 2.70 mol, 0.2 eq) was added. After 12 h, the reaction mixture was concentrated under reduced pressure to remove acetonitrile (15.0 L). The residue was cooled to 10° C. and filtered. The filter cake was washed with a minimal amount of acetonitrile and $H_2O$, until the pH of filtrate was 7, then it was dried in vacuum to give 2461 g (64.1%) of (3R,4R,5R)-5-(2,4-dioxo-1,2,3,4-tetrahydropyrimidin-1-yl)-4-fluoro-4-methyl-2-methylideneoxolan-3-yl acetate as a white solid.

To a solution of (3R,4R,5R)-5-(2,4-dioxo-1,2,3,4-tetrahydropyrimidin-1-yl)-4-fluoro-4-methyl-2-methylideneoxolan-3-yl acetate (2461 g, 8.662 mol, 1.0 eq) in methanol (12.30 L) was added sodium methoxide (30% in methanol, 77.97 g, 0.433 mol, 0.05 eq). The reaction mixture was stirred at 50° C. for 15 h. Based on HPLC, an additional amount of the sodium methoxide (30% in methanol, 77.97 g, 0.433 mol, 0.05 eq) was added. After 8 h more, the reaction was completed and then cooled to 5° C. After being stirred at 5° C. for 12 h, the precipitated product was collected by filtration, the filter cake was washed with a minimal amount of methanol, dried in vacuum to give 1856 g (88.4%) of 1-[(2R,3R,4R)-3-fluoro-4-hydroxy-3-methyl-5-methylideneoxolan-2-yl]-1,2,3,4-tetrahydropyrimidine-2,4-dione 2 as an off-white solid. $^1$H NMR (400 MHz, DMSO-d$_6$) δ(ppm): 11.56 (s, 1H), 7.39 (s, 1H), 6.16-6.12 (d, 1H), 5.98 (s, 1H), 5.68-5.66 (s, 1H), 4.63-4.53 (m, 2H), 4.28 (s, 1H), 1.37-1.31 (d, 3H).

Step 2: Preparation of 1-((2R,3R,4S,5R)-3,5-difluoro-4-hydroxy-5-(iodomethyl)-3-methyl-tetrahydrofuran-2-yl)pyrimidine-2,4(1H,3H)-dione 21

To a solution of 1-[(2R,3R,4R)-3-fluoro-4-hydroxy-3-methyl-5-methylideneoxolan-2-yl]-1,2,3,4-tetrahydropyrimidine-2,4-dione 2 (1855 g, 7.66 mol, 1.0 eq) and TEA.3HF (1976 g, 12.254 mol, 1.6 eq) in DCM (37 L) was added N-Iodosuccinimide (3274 g, 14.552 mol, 1.9 mol). The reaction mixture was stirred at 25° C. for 24 h. Then 10% aqueous NaHSO$_3$ (13 L) was added and the mixture was stirred for 2 h. The precipitated product was collected by filtration. The filter cake was combined with another batch (starting with 1555 g of 0001289-015-01). The combined solids were washed with a minimal amount of DCM, 5% aqueous NaHCO$_3$ until the pH of filtrate was 7-8 and H$_2$O, dried in vacuum to give 5060 g (92.6%) of crude product as a light yellow solid. A mixture of the crude product (2500 g) in methanol (37.5 L) was heated to reflux for 2 h and then cooled to 5° C. After being stirred at 5° C. for 2 h, the precipitated product was collected by filtration, the filter cake was washed with a minimal amount of methanol, dried to give 1970 g (78.8%) of 1-((2R,3R,4S,5R)-3,5-difluoro-4-hydroxy-5-(iodomethyl)-3-methyltetrahydrofuran-2-yl) pyrimidine-2,4(1H,3H)-dione 21 as a light yellow solid.

$^1$H NMR (400 MHz, DMSO-d$_6$) $\delta_H$ 11.63 (s, 1H), 7.81-7.51 (m, 1H), 6.31-5.95 (m, 2H), 5.73-5.71 (d, 1H), 4.56-3.78 (m, 3H), 1.30-1.25 (m, 3H).

Step 3: Preparation of (2R,3S,4R,5R)-5-(2,4-dioxo-3,4-dihydropyrimidin-1(2H)-yl)-2,4-difluoro-2-(iodomethyl)-4-methyltetrahydrofuran-3-yl Isobutyrate, 22

To a stirred suspension of 1-((2R,3R,4S,5R)-3,5-difluoro-4-hydroxy-5-(iodomethyl)-3-methyltetrahydrofuran-2-yl) pyrimidine-2,4(1H,3H)-dione 21 (400 g, 1.03 mol, 1 eq.) in EtOAc (2 L) was added at ambient temperature 4-dimethylaminopyridine (6.30 mg, 51.5 mmol, 5 mol %) and triethylamine (172 mL, 1.24 mol). The resulting suspension was cooled to 0° C. and isobutyryl chloride (130 mL, 1.24 mol, 1.2 eq.) added dropwise over 40 min, maintaining the temperature <10° C. The reaction mixture was stirred at ambient temperature for 3 h. Water (1 L) and EtOAc (300 mL) was added to the reaction mixture, and the phases separated. The aqueous layer was subsequently extracted with EtOAc (2 L). The organic layers were combined, dried over MgSO$_4$ and SiO$_2$, and filtered. The filter cake was washed with EtOAc (300 mL) and the filtrate concentrated in vacuo at 40° C. to give (2R,3S,4R,5R)-5-(2,4-dioxo-3,4-dihydropyrimidin-1(2H)-yl)-2,4-difluoro-2-(iodomethyl)-4-methyltetrahydrofuran-3-yl isobutyrate, 22, as a white solid (461 g, 98% yield). $^1$H NMR (CDCl$_3$, 300 MHz) $\delta_H$ 8.59 (br s, 1H), 7.30 (br d, 1H), 5.83 (dd, 1H), 3.71-3.38 (m, 2H), 2.77 (sept, 1H), 1.45 (d, 3H), 1.26 (d, 3H). ES$^+$ m/z 459 MH$^+$

Step 4: Preparation of ((2S,3S,4R,5R)-5-(2,4-dioxo-3,4-dihydropyrimidin-1(2H)-yl)-2,4-difluoro-3-(isobutyryloxy)-4-methyltetrahydrofuran-2-yl) methyl 3-chlorobenzoate 23

To a stirred mixture of (2R,3S,4R,5R)-5-(2,4-dioxo-3,4-dihydropyrimidin-1(2H)-yl)-2,4-difluoro-2-(iodomethyl)-4-methyltetrahydrofuran-3-yl isobutyrate 22 (461 g, 1.01 mol, 1 eq.) and 3-chlorobenzoic acid (173 g, 1.11 mol, 1.1 eq.), dipotassium hydrogen phosphate (364 g, 2.09 mol, 2.08 eq.), and tetra-n-butylammonium sulfate (345 g, 1.02 mol, 1.07 eq.) in EtOAc (3.5 L) and water (900 mL) at 0° C. was added 3-chloroperoxybenzoic acid (966 g, 3.92 mol, 3.9 eq., 70% w/w) portion-wise over 20 min. The mixture was warmed to 18° C. and stirred for 16 h. The mixture cooled to 0° C., followed by dropwise addition of Na$_2$SO$_3$ (2.4 L, 10% aq.) over 30 min such that the internal temperature was kept <5° C. The phases were separated, and the organic phase washed with Na$_2$SO$_3$ (2×2 L, 10% aq.), NaHCO$_3$ (4×2 L, sat. aq.), brine (2 L) and dried over MgSO$_4$ and SiO$_2$ and filtered. The filtrate was concentrated in vacuo at 40° C. to give a gum.

The material was dissolved in EtOAc (1.2 L). NaHCO$_3$ (800 mL, sat. aq.) was added to the reaction mixture and stirred for 24 h. The organic phase was then separated, and washed with NaHCO$_3$ (sat. aq.), brine, dried over MgSO$_4$ and concentrated under in vacuo at 40° C. to give an orange gum. The material was re-dissolved in EtOAc and SiO$_2$ was added. The mixture was stirred for 15 min, and then filtered through a pad of SiO$_2$. The filter cake was washed with EtOAc and concentrated under in vacuo at 40° C. to give ((2S,3S,4R,5R)-5-(2,4-dioxo-3,4-dihydropyrimidin-1(2H)-yl)-2,4-difluoro-3-(isobutyryloxy)-4-methyl-tetrahydrofuran-2-yl)methyl 3-chlorobenzoate 23 as an orange gum (426 g, 87% yield). $^1$H NMR (CDCl$_3$, 300 MHz) $\delta_H$ 8.96 (s, 1H), 8.00 (s, 1H), 7.92 (d, 1H), 7.58 (d, 1H), 7.43 (t, 1H), 7.20 (d, 1H), 5.67 (m, 1H), 4.61 (dq, 2H), 2.74 (sept, 1H), 1.44 (d, 3H), 1.25 (d, 3H). ES$^-$ m/z 485 M-H Step 5: Preparation of ((2S,3S,4R,5R)-2,4-difluoro-3-(isobutyryloxy)-4-methyl-5-(2-oxo-4-(1H-1,2,4-triazol-1-yl)pyrimidin-1(2H)-yl)tetrahydrofuran-2-yl)methyl 3-chlorobenzoate, 24

To a stirred mixture of ((2S,3S,4R,5R)-5-(2,4-dioxo-3,4-dihydropyrimidin-1(2H)-yl)-2,4-difluoro-3-(isobutyryloxy)-4-methyltetrahydrofuran-2-yl)methyl 3-chlorobenzoate 23 (1.02 g, 210 mmol, 1 eq.) and triazole (144 g, 2.10 mol, 10 eq.) in CH$_2$Cl$_2$ (1 L) at ambient temperature was added Et$_3$N (291 mL, 2.10 mol, 10 eq.). The resulting mixture was cooled to 0° C., and phosphorous(V) oxychloride (49.0 mL, 524 mmol, 2.5 eq.) was added dropwise maintaining the temperature <10° C. The mixture was stirred at 0° C. for 3 h. The mixture was added to water and extracted into CH$_2$Cl$_2$. The organic phases were combined, dried over MgSO$_4$, filtered and solvent concentrated in vacuo at 40° C. to give ((2S,3S,4R,5R)-2,4-difluoro-3-(isobutyryloxy)-4-methyl-5-(2-oxo-4-(1H-1,2,4-triazol-1-yl)pyrimidin-1(2H)-yl)tetrahydro-furan-2-yl)methyl 3-chlorobenzoate, 24, as an orange oil (118 g, quant.). $^1$H NMR (CDCl$_3$, 300 MHz) $\delta_H$ 9.25 (s, 1H), 8.14 (s, 1H), 8.01-7.80 (m, 3H), 7.62 (d, 1H), 7.64 (t, 1H), 4.68 (m, 1H), 2.76 (m, 1H), 1.45 (br d, 3H), 1.30-1.15 (m, 6H). ES$^+$ m/z 538 MH$^+$ Step 6: Preparation of 4-amino-((2R,3R,4S,5S)-3,5-difluoro-4-hydroxy-5-(hydroxymethyl)-3-methyltetrahydrofuran-2-yl)pyrimidin-2(1H)-one, 25

To a stirred mixture of ((2S,3S,4R,5R)-2,4-difluoro-3-(isobutyryloxy)-4-methyl-5-(2-oxo-4-(1H-1,2,4-triazol-1-yl)pyrimidin-1(2H)-yl)tetrahydrofuran-2-yl)methyl 3-chlorobenzoate 24 in THF (1 L) at ambient temperature was added NH$_3$ (200 mL, conc. aq.). The mixture was stirred for 16 h at ambient temperature. The mixture was concentrated in vacuo at 40° C. To the resulting slurry was added MeOH (250 mL) and NH$_3$ (250 mL, 7N in MeOH), and the mixture stirred at ambient temperature for 2 h. The mixture was concentrated in vacuo at 40° C. to give an orange gum. EtOAc was added, and the mixture stirred for 16 h at ambient temperature. The resulting solid was collected by filtration, and washed with EtOAc (500 mL) and Et$_2$O (500 mL) to give 4-amino-1-((2R,3R,4S,5S)-3,5-difluoro-4-hydroxy-5-(hydroxymethyl)-3-methyltetrahydrofuran-2-yl)pyrimidin-2(1H)-one, 25, as an off-white solid (57.0 g, 65% yield). $^1$H NMR (MeOD, 300 MHz) $\delta_H$ 7.82 (br s, 1H), 6.52 (br d, 1H), 5.89 (d, 1H), 4.07 (br t, 1H), 1.30 (d, 1H).

Reference 2

Synthesis of 1-((2R,3R,4 S,5 S)-3,5-difluoro-4-hydroxy-5-(hydroxymethyl)-3-methyl-tetrahydrofuran-2-yl)pyrimidine-2,4(1H, 3H)-dione 4

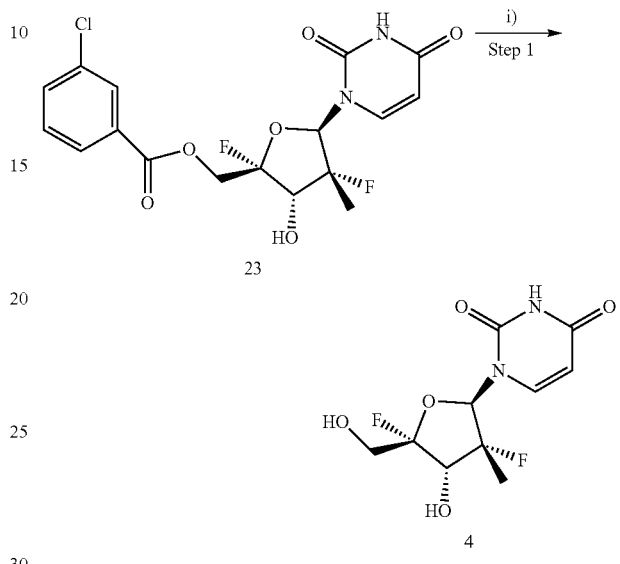

1) NH$_3$/MeOH

To a solution of ((2S,3S,4R,5R)-5-(2,4-dioxo-3,4-dihydropyrimidin-1(2H)-yl)-2,-difluoro-3-(isobutyryloxy)-4-methyltetrahydrofuran-2-yl)methyl 3-chlorobenzoate 23 (238 g, 489 mmol) in MeOH (100 mL) was added NH$_3$ (1 L, 7N in MeOH). The mixture was stirred at ambient temperature for 16 h. The mixture was concentrated in vacuo. The resulting oil was stirred in CH$_2$Cl$_2$ (200 mL) for 1 h, and the resulting solid collected by filtration, washed with Et$_2$O and dried in vacuo at 50° C. for 48 h. 1-((2R,3R,4S,5S)-3,5-difluoro-4-hydroxy-5-(hydroxymethyl)-3-methyltetrahydrofuran-2-yl)pyrimidine-2,4(1H,3H)-dione, 4, was obtained as an off-white solid (102 g, 75% yield). $^1$H NMR (MeOD, 300 MHz) $\delta_H$ 7.80 (d, 1H), 6.45 (br d, 1H), 5.71 (d, 1H), 4.15 (br m, 1H), 3.77 (m, 2H), 1.37 (d, 1H). $^{19}$F NMR (MeOD, 283 MHz) $\delta_F$ −135 (m, 1F), −159 (m, 1F). ES$^+$ m/z 279 MH$^+$ Example 1

Syntheis of isopropyl ((S)-(((2S,3 S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate I-1

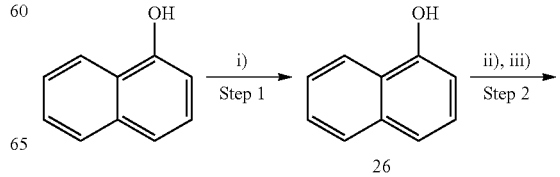

-continued

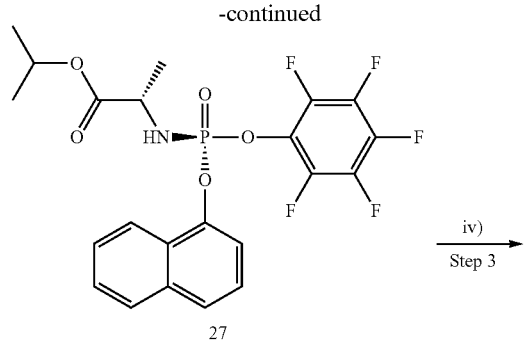

27

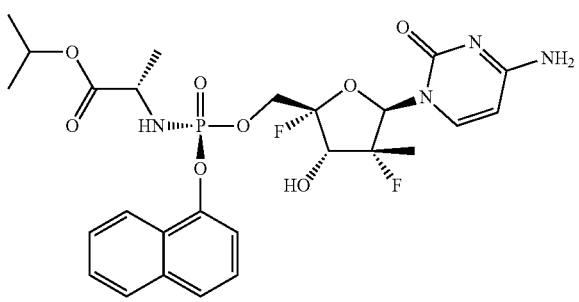

I-1 i) Et₃N, POCl₃, Et₂O; ii) isopropyl L-alanine, Et₃N, CH₂Cl₂; iii) C₆F₅OH, Et₃N, CH₂Cl₂; iv) 25, tBuMgCl, DMF Step 1: Preparation of naphthalen-1-yl Phosphorodichloridate 26

To a stirred solution of phosphorus (V) oxychloride (30.1 mL, 327 mmol, 1 eq.) in diethyl ether (500 mL) at −78° C. under argon was added 1-napthol (47.1 g, 327 mmol, 1 eq.). Triethylamine (45.0 mL, 327 mmol, 1 eq.) was added drop-wise over 2 h maintaining the temperature <−60° C. The reaction mixture was allowed to warm to ambient temperature over 2 h, then stirred for 16 h. The mixture was filtered through Celite, and the filter cake washed with diethyl ether to give a colorless solution. The filtrate was concentrated under reduced pressure (distillation temperature 25° C.) to give naphthalen-1-yl phosphorodichloridate 26 (78.2 g, 92% yield) as a yellow oil. $^{31}$P NMR (CDCl₃, 161 MHz) δ$_p$ 4.44 (s).

Step 2: Preparation of Isopropyl ((R)-(naphthalen-1-yloxy)(perfluorophenoxy)phosphoryl)-L-alaninate 27

To a stirred solution of naphthalen-1-yl phosphorodichloridate 26 (78.2 g, 299 mmol, 1 eq.) and isopropyl-L-alanine (41.9 g, 299 mmol, 1 eq.) in dichloromethane at −78° C. under argon was added triethylamine (43 mL, 589 mmol, 2 eq.) drop-wise maintaining the temperature <−70° C. The reaction mixture was stirred at −78° C. for 30 min, then at 0° C. for 30 min.

Pentafluorophenol (66.0 g, 359 mmol, 1.2 eq.) and triethylamine (43 mL, 589 mmol, 2 eq.) were stirred in dichloromethane (100 mL), and this mixture was added drop-wise to the bulk reaction mixture. After 1 h, the reaction mixture was concentrated under reduced pressure to give a white solid. The solid was suspended in ethyl acetate/heptane (1:1, 300 mL) and silica added. The mixture was stirred for 5 min then filtered. The filter cake was washed with ethyl acetate/heptane (1:1, 200 mL). The filtrate was concentrated under reduced pressure. The resulting residue was suspended in 1:4 ethyl acetate:heptane (500 mL,) and stirred for 16 h at ambient temperature. Precipitates was collected by filtration to give isopropyl ((R)-(naphthalen-1-yloxy)-(perfluorophenoxy)phosphoryl)-L-alaninate 26 (49.2 g, 32%, >99:1 d.r.) as a white solid. $^1$H NMR (CDCl₃, 300 MHz): 8.10-8.13 (m, 1H), 7.87 (dd, 1H), 7.71 (d, 1H), 7.51-7.61 (m, 3H), 7.42 (t, 1H), 4.95-5.03 (m, 1H), 4.14-4.27 (m, 1H), 3.98-4.06 (m, 1H), 1.42 (q, 3H), 1.18-1.25 (m, 6H). $^{31}$P NMR (CDCl₃, 122 MHz): −0.05 (s). $^{19}$F NMR (CDCl₃, 238 MHz): −152.54-−153.40 (d, 1F), −158.86-−159.61 (t, 1F), −161.62-−162.30 (t, 1F)

Step 3: Preparation of ((S)-(((2R,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate I-1

To a stirred solution of 4-amino-1-((2R,3R,4S,5S)-3,5-difluoro-4-hydroxy-5-(hydroxymethyl)-3-methyltetrahydrofuran-2-yl)pyrimidin-2(1H)-one (13.9 g, 50.1 mmol, 1 eq.) in dimethylformamide (70 mL) under argon at −10° C. was added tert-butylmagnesium chloride (1M in THF, 100 mL, 100 mmol, 2 eq.) drop-wise over 30 min maintaining internal temperature <10° C. The reaction mixture was stirred for 20 min at −5° C., and isopropyl ((R)-(perfluorophenoxy)(naphoxy)phosphoryl)-L-alaninate (37.8 g, 75.1 mmol, 1.5 eq.) was then added. The reaction mixture was stirred at −5° C. for 3 h, and added to ammonium chloride (sat aq., 200 mL) and 2-MeTHF (200 mL). The phases were separated, and the aqueous phase extracted with 2-methyltetrahydrofuran. The organic phases were combined, and dried over magnesium sulfate, filtered and solvent removed under reduced pressure. The resulting oil was purified by dry flash chromatography (silica, 2.5-10% methanol/dichloromethane) to give an orange oil. Fractions containing product was then purified by Isolera (120 g ZIP SPHERE, silica, eluting 5-7.5% methanol/dichloromethane). Clean fractions were dissolved in water/acetonitrile and freeze-dried to give isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate I-1 (3.16 g) as an off-white solid. $^1$H NMR (DMSO-d₆ with D₂O, 400 MHz): 8.03 (m, 1H), 7.90 (m, 1H), 7.71 (m, 1H), 7.55-7.52 (m, 2H), 7.43-7.37 (m, 2H), 7.11 (m, 1H), 6.41 (br d, 1H), 5.58-5.50 (m, 1H), 4.77 (sept, 1H), 4.28 (m, 2H), 3.99 (t, 1H), 1.22-1.02 (m, 12H); $^{19}$F NMR (DMSO-d₆, 376 MHz): −123 (m, 1F) −154 (m, 1F); $^{31}$P NMR (DMSO-d₆, 161 MHz): 4.74 (s). ES⁺ m/z 597 MH⁺

Example 2

Synthesis of Isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate I-3

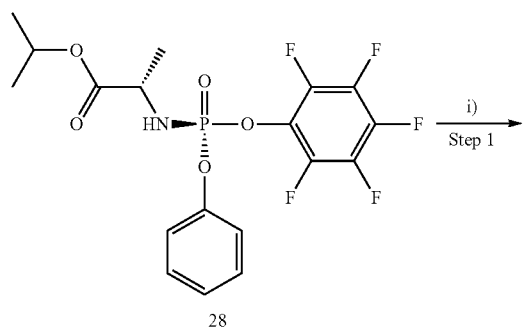

28

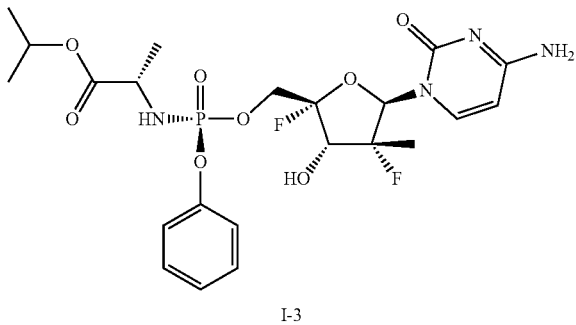

I-3 i) 25, tBuMgCl, DMF

To a stirred solution of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (41 g, 134 mmol, 1.0 eq.) in anhydrous dimethylformamide (410 mL) under argon held at 0° C. was added $^t$BuMgCl (296 mL of a 1.0 M solution in tetrahydrofuran, 300 mmol, 2.0 eq.) over 30 minutes maintaining an internal temperature below 10° C. The resulting mixture was stirred for at 0° C. for 10 minutes then isopropyl ((S)-(perfluorophenoxy)(phenoxy)phosphoryl)-L-alaninate 28 (134 g, 300 mmol, 2.0 eq.) was added as a solid. The resulting mixture was stirred at 0° C. for 10 minutes then warmed to ambient temperature over 1 h. The resulting mixture was stirred at ambient temperature for 30 minutes then re-cooled to 0° C. The reaction mixture was diluted with 2-methyltetrahydrofuran (400 mL) and then quenched by addition of ammonium chloride then further diluted with water and ethyl acetate. Celite (~75 g) was added and the mixture was filtered rinsing the filter cake with water and ethyl acetate. The layers were separated and the aqueous layer was extracted with ethyl acetate. The combined ethyl acetate extracts were washed with sodium hydrogen carbonate (sat. aqueous solution) and the sodium hydrogen carbonate aqueous back extracted with ethyl acetate. The combined ethyl acetate extracts were dried over magnesium sulfate, filtered and concentrated under reduced pressure to give a brown oil. The oil was re-dissolved in ethyl acetate and washed with sodium hydrogen carbonate (sat. aqueous solution diluted to 1.0 L with water). The sodium hydrogen carbonate aqueous was back extracted with ethyl acetate and the combined ethyl acetate extracts were dried over magnesium sulfate, filtered and concentrated under reduced pressure to give the crude product (113 g) as a brown oil. The crude was purified by repeated dry flash column chromatography on silica with either ethyl acetate-methanol (0-15%) then dichloromethane-methanol (0-10%) mixtures to give an off-white foam which was freeze dried from water-acetonitrile (35%) to give isopropyl ((S)-(((2S,3S,4R,5R)-5-(4-amino-2-oxopyrimidin-1(2H)-yl)-2,4-difluoro-3-hydroxy-4-methyl-tetrahydrofuran-2-yl)methoxy)(phenoxy)phosphoryl)-L-alaninate I-3 (27.3 g) as an off-white amorphous solid and as a 95:5 mixture of diastereoisomers. $^1$H NMR (DMSO-d$_6$, 400 MHz): 7.38-7.27 (br m, 5H), 7.21-7.16 (m, 3H), 6.45 (d, 1H), 6.12 (br s, 2H), 5.70 (d, 1H), 4.83 (septet, 1H), 4.24 (br s, 2H), 4.04 (br td, 1H), 3.79 (br s, 1H), 1.20 (d, 3H), 1.17 (d, 3H), 1.11 (d, 6H). $^{19}$F NMR (DMSO-d$_6$, 376 MHz): −120.3 and −122.9 (br s 1F), −148.5 and −154.7 (br s, 1F). $^{31}$P NMR (DMSO-d$_6$, 161 MHz): 4.22 (s). ES$^+$546.97.

Example 3

Synthesis of Cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate

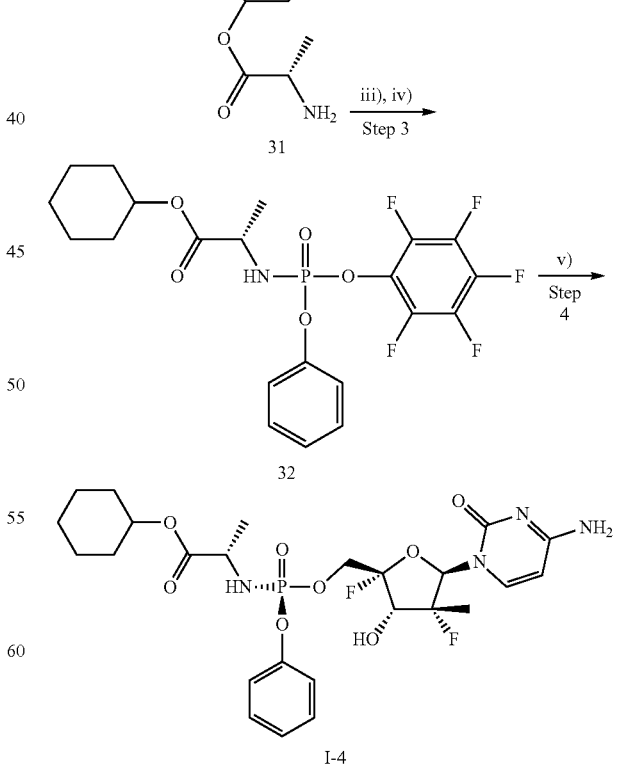

I-4 i) EDCl, DMAP, Et$_3$N, CH$_2$Cl$_2$; TFA, CH$_2$Cl$_2$; iii) P(O)(OPh)Cl$_2$, Et$_3$N, CH$_2$Cl$_2$;
iv) C$_6$F$_5$OH, Et$_3$N, CH$_2$Cl$_2$; v) 25, tBuMgCl, DMF

Step 1: Preparation of Cyclohexyl (tert-butoxycarbonyl)-L-alaninate 30

To a stirred solution of (tert-butoxycarbonyl)-L-alanine (5 g, 26.4 mmol, 1 eq.), 4-(dimethylamino)pyridine 29 (323 mg, 2.64 mmol, 10 mol %) and Et$_3$N (14.7 mL, 106 mmol, 4 eq.) in CH$_2$Cl$_2$ (50 mL) was added N-(3-dimethylaminopropyl)-N'-ethylcarbodiimide hydrochloride (10.1 g, 52.9 mmol, 2 eq.). The reaction mixture was stirred at 0° C. for 1 h. Cyclohexanol (3.35 mL, 31.7 mmol, 1.2 eq.) was added, and the reaction mixture stirred for 48 h at ambient temperature. The reaction mixture was concentrated in vacuo to give an oily solid which was partitioned with Et$_2$O and water. The phases were separated and the organic phase washed with water (50 mL), brine (50 mL), dried over MgSO$_4$, filtered and concentrated in vacuo to give a colorless oil. Purificationby flash chromatography (SiO$_2$, eluting 11-14% EtOAc/heptane) gave cyclohexyl (tert-butoxycarbonyl)-L-alaninate, 30, (1.76 g, 25% yield). $^1$H NMR (CDCl$_3$, 300 MHz) $\delta_H$ 5.04 (br s, 1H), 4.83-4.76 (m, 1H), 4.27 (br quint, 1H), 1.84 (br s, 2H), 1.72 (br s, 2H), 155-1.23 (m, 6H), 1.37 (d, 3H).

Step 2: Preparation of Cyclohexyl L-alaninate, 31

To a stirred solution of cyclohexyl (tert-butoxycarbonyl)-L-alaninate 30 (1.76 g, 6.49 mmol, 1 eq.) in CH$_2$Cl$_2$ (18 mL) at 0° C. was added trifluoroacetic acid (2 mL). The reaction mixture was stirred at ambient temperature for 2 h, then left to stand for 16 h. The reaction mixture was added to NaHCO$_3$ (70 mL, sat. aq.). The phases were separated, and the aqueous phase extracted with CH$_2$Cl$_2$. The organic phases were combined and dried over MgSO$_4$, filtered and concentrated in vacuo to give cyclohexyl L-alaninate, 31, as a yellow oil (1.179 g, 100% yield). $^1$H NMR (CDCl$_3$, 300 MHz) $\delta_H$ 4.77 (m, 1H), 3.51 (m, 1H), 1.83-0.85 (m, 13H).

Step 3: Preparation of Cyclohexyl ((perfluorophenoxy)(phenoxy)phosphoryl)-L-alaninate, 32

To a solution of phenyl phosphorodichloridate (1.23 g, 5.84 mmol, 1 eq.) in CH$_2$Cl$_2$ (10 mL) at −78° C. under Ar was added a solution of cyclohexyl L-alaninate 31 (1 g, 5.84 mmol) and Et$_3$N (0.81 mL, 5.84 mmol, 1 eq.) in CH$_2$Cl$_2$ (5 mL). The reaction mixture was stirred at −78° C. for 30 min and then warmed to ambient temperature. The mixture was cooled to 0° C., and a solution of pentafluorophenol (1.07 g, 5.84 mmol, 1 eq.) in CH$_2$Cl$_2$ (5 mL), followed by Et$_3$N (0.81 mL, 5.84 mmol, 1 eq.). The reaction mixture was stirred at 0° C. for 2 h then at ambient temperature for 16 h. The mixture was concentrated in vacuo to give a white solid. The solid was suspended in EtOAc/heptane (1:1, 100 mL) and SiO$_2$ (5 g) added. The mixture was stirred at ambient temperature for 5 min, and filtered. The filter cake was washed with EtOAc/heptane (1:1, 200 mL). The filtrate was concentrated in vacuo to give a white solid. Purified by flash chromatography (SiO$_2$, eluting 20% EtOAc/heptane) to give cyclohexyl ((perfluorophenoxy)(phenoxy)phosphoryl)-L-alaninate 32 (1.62 g, 56% yield).

Step 4: Preparation of Cyclohexyl ((S)-(2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate, I-4

To a stirred suspension of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (284 mg, 1.02 mmol, 1 eq.) in dry THF (6 mL) under Argon at 0° C. was added $^t$BuMgCl (1.28 mL, 1.28 mmol, 2 eq., 1M in THF). To the reaction mixture was added cyclohexyl ((((R)-1-(cyclohexyloxy)-1-oxopropan-2-yl)amino)(perfluorophenoxy)phosphoryl)-L-alaninate (632 mg, 1.28 mmol) and the reaction mixture was stirred at 0° C. for 2 h. The reaction mixture was added to NH$_4$Cl (10 mL, sat. aq.), and extracted into 2-MeTHF. The combined organic phases were dried over MgSO$_4$, filtered and the concentrated in vacuo to give a brown oil. Purification by flash chromatography (SiO$_2$, eluting 10-15% MeOH/CH$_2$Cl$_2$) gave a yellow foam which was purified by MDAP (XSelect C18, eluting 30% MeCN/water). Fractions containing product was freeze dried to give cyclohexyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate, (R$_P$), (14 mg, 2%) and cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate, Target I-4 (S$_P$), (49 mg, 8%) as white solids.

R$_P$ Diastereomer: $^1$H NMR (DMSO-d$_6$, 400 MHz) $\delta_H$ 7.40-7.20 (br m, 3H), 7.19-7.10 (br m, 3H), 6.45 (d, 1H), 6.21-6.10 (br m, 2H), 5.70 (d, 1H), 4.60 (br s, 1H), 4.30-4.20 (br m, 2H), 3.96 (br td, 1H), 3.78 (br q, 1H), 1.68 (s, 2H), 1.60 (br s, 2H), 1.43 (br s, 1H), 1.35-br m, 5H), m 1.19 (d, 3H), 1.18/1.12 (s, 3H, rotameric); $^{19}$F NMR (DMSO-d$_6$, 376 MHz) $\delta_F$ (rotameric)-120.1-−120.3/−122.4-−122.7 (br m, 1F), −148.3-−148.6/−154.7-−155.0 (br m, 1F); $^{31}$P NMR (DMSO-d$_6$, 161 MHz) $\delta_P$ 4.18 (s). UPLC (Acid, 2-95%, CSH C18) RT=2.101 min, 98.94% ESIpos m/z 587 MH$^+$ S$_P$ Diastereomer (I-4): $^1$H NMR (DMSO-d$_6$, 400 MHz) $\delta_H$ 7.40-7.27 (br m, 5H), 7.22-7.10 (br m, 3H), 6.47 (d, 1H), 6.19-6.12 (br m, 2H), 5.71 (d, 1H), 4.61 (br s, 1H), 4.25 (br s, 2H), 4.04 (br td, 1H), 3.87-3.75 (br m, 1H), 1.67 (br s, 2H), 1.61 (br s, 2H), 1.43 (br s, 1H), 1.38-1.25 (br m, 5H), 1.23/1.15 (s, 3H, rotameric) 2.21 (d, 3H). $^{19}$F NMR (DMSO-d$_6$, 376 MHz) $\delta_F$ (rotameric) −120.3/−123.0 (s m, 1F), 148.5/−154.5-−154.8 (br m, 1F). $^{31}$P NMR (DMSO-d$_6$, 161 MHz) $\delta_P$ 4.21 (s). UPLC (Acid, 2-95%, CSH C18) RT=2.12 min, 99.49% ESIpos m/z 587 MH$^+$

Example 4

Synthesis of pentan-3-yl ((S/R$_P$)-(((2S,3 S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate

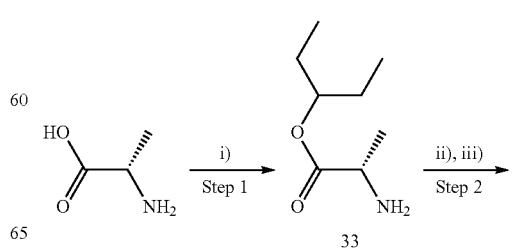

33

-continued

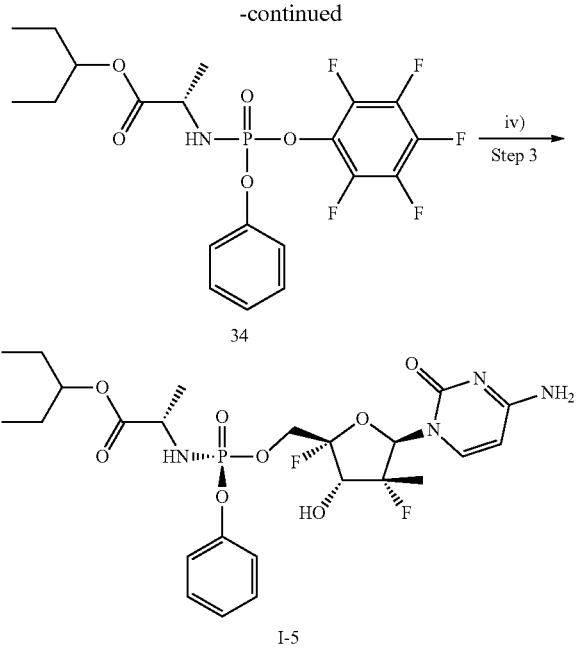

iii) 3-pentanol, SOCl$_2$,; ii) P(O)(OPh)Cl$_2$, Et$_3$N, CH$_2$Cl$_2$; iii) C$_6$F$_5$OH, Et$_3$N, CH$_2$Cl$_2$
iv) 25, tBuMgCl, DMF Step 1: Preparation of pentan-3-yl L-alaninate, 33

To a stirred solution of 3-pentanol (15.2 mL, 140 mmol, 2.5 eq.) and L-alanine (5 g, 56.1 mmol, 1 eq.) added thionyl chloride (6.1 mL, 84.2 mmol, 1.5 eq.) at ambient temperature. The reaction mixture was heated to reflux for 24 h, then cooled to ambient temperature. The mixture was added to a vigorously stirred mixture of CH$_2$Cl$_2$ and NaHCO$_3$ (sat. aq.). This mixture was stirred for 15 min and then the phases separated. The aqueous phase was washed with CH$_2$Cl$_2$ and the organic phases combined, dried over MgSO$_4$, filtered and concentrated in vacuo. The resulting oil was azeotroped with toluene and EtOAc to give pentan-3-yl L-alaninate, 33, (905 mg, 10%) as a pale brown oil. $^1$H NMR (CDCl$_3$, 300 MHz) $\delta_H$ 4.77 (quint, 1H), 3.53 (q, 1H), 1.62-1.52 (m, 4H), 1.34 (d, 1H), 0.87 (t, 6H).

Step 2:—Preparation of pentan-3-yl ((perfluorophenoxy)(phenoxy)phosphoryl)-L-alaninate, 34

To a solution of phenyl phosphorodichloridate (1.2 g, 5.68 mmol, 1 eq.) in CH$_2$Cl$_2$ (4 mL) at −78° C. under Ar was added a solution of pentan-3-yl L-alaninate (905 mg, 5.84 mmol) in CH$_2$Cl$_2$ (12 mL). Et$_3$N (0.79 mL, 5.68 mmol, 1 eq.) was added. The reaction mixture was stirred at −78° C. for 1 h and then warmed to ambient temperature. The mixture was cooled to 0° C., and a solution of pentafluorophenol (1.05 g, 5.68 mmol, 1 eq.) in CH$_2$Cl$_2$ (4 mL), followed by Et$_3$N (1.58 mL, 11.4 mmol, 2 eq.). The reaction mixture was stirred at 0° C. for 15 min then at ambient temperature for 2 h. The mixture was concentrated in vacuo to give a white solid. The solid was suspended in EtOAc/heptane (1:1, 100 mL) and SiO$_2$ (5 g) added. The mixture was stirred at ambient temperature for 5 min, and filtered. The filter cake was washed with EtOAc/heptane (1:1, 200 mL). The filtrate was concentrated in vacuo to give pentan-3-yl ((perfluorophenoxy)-(phenoxy)phosphoryl)-L-alaninate, 34, (1.9 g, 69% yield) as a white solid (as a 1:1 mixture of diastereomers). $^1$H NMR (CDCl$_3$, 300 MHz) $\delta_H$ 7.36 (t, 2H), 7.29-7.19 (m, 3H), 4.81 (sextet, 1H), 4.24-4.15 (m, 1H), 4.07-3.94 (m, 1H), 1.62-1.55 (m, 4H), 1.48 (d, 1.5H), 1.47 (d, 1.5H), 0.90-0.84 (m, 6H). $^{31}$P NMR (CDCl$_3$, 122 MHz) $\delta_P$ −0.99 (s).

Step 3: Preparation of pentan-3-yl (((((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate I-5

To a stirred suspension of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (265 mg, 0.955 mmol, 1 eq.) in dry THF (6 mL) under Argon at 0° C. was added $^t$BuMgCl (1.43 mL, 1.28 mmol, 1.5 eq., 1M in THF). To the mixture was added pentan-3-yl ((perfluorophenoxy)(phenoxy)phosphoryl)-L-alaninate 34 (690 mg, 1.43 mmol) and the reaction mixture was stirred at 0° C. for 1.5 h. The reaction mixture was added to NH$_4$Cl (10 mL, sat. aq.), and extracted into EtOAc. The organic phase was washed with NaHCO$_3$ (sat. aq.), brine, dried over MgSO$_4$, filtered and the concentrated in vacuo to give a brown oil. Purified by MDAP (XSelect C18, MeCN/water). Fractions containing product freeze dried to give pentan-3-yl (((((2S,3S,4R,5R)-5-(4-amino-2-oxopyrimidin-1(2H)-yl)-2,4-difluoro-3-hydroxy-4-methyltetrahydrofuran-2-yl)methoxy)-(phenoxy)phosphoryl)-L-alaninate, I-5, (156 mg, 28% yield, mixture of epimers) as a white solid. $^1$H NMR (DMSO-d$_6$, 400 MHz) $\delta_H$ 7.43-7.08 (m, 7H), 6.49 (d, 1H), 6.23-6.09 (m, 2H), 5.70 (d, 1H), 4.61 (m, 1H), 4.24 (m, 2H), 4.03 (t, 1H), 3.80 (m, 1H), 1.54 (m, 3H), 1.30-1.00 (m, 5H), 0.82-0.70 (m, 6H). $^{19}$F NMR (DMSO-d$_6$, 376 MHz) $\delta_F$ −120 (m), −122 (m), −123.0 (m), −148 (m), −154 (m). $^{31}$P NMR (DMSO-d$_6$, 161 MHz) $\delta_P$ 4.25 (s). UPLC (Acid, 2-95%, CSH C18) RT=2.489 min, 19.65% ESIpos m/z 587 MH$^+$R$_P$, RT=2.610 min, 69.11% ESIpos m/z 587 MH$^+$ Example 5

Synthesis of Isopropyl (2 S)-2-[[[(2S,3 S,4R,5R)-5-(4-amino-2-oxo-pyrimidin-1-yl)-2,4-difluoro-3-hydroxy-4-methyl-tetrahydrofuran-2-yl]methoxy-[[(1S)-2-isopropoxy-1-methyl-2-oxo-ethyl]amino]phosphoryl]amino]propanoate, I-6

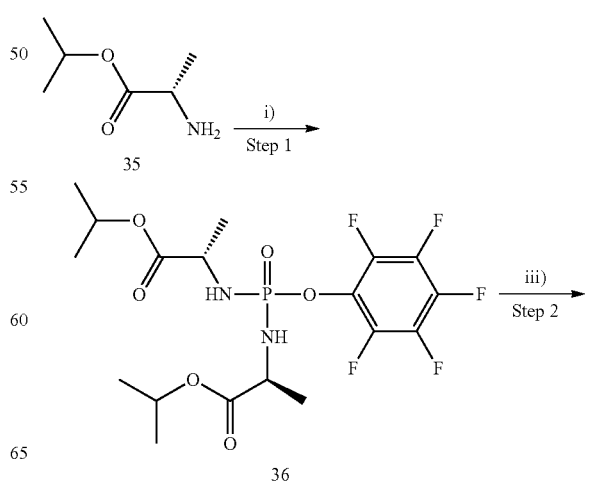

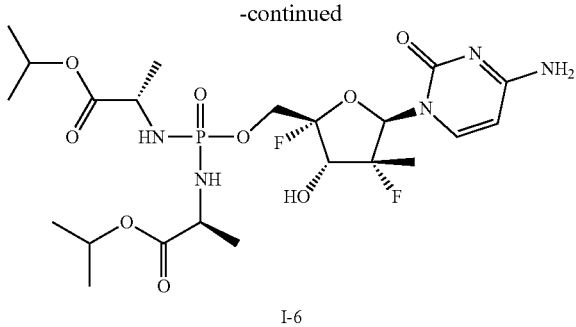

I-6 i) POCl₃, Et₃N, CH₂Cl₂; ; ii) C₆F₅OH, Et₃N, CH₂Cl₂ iii) 25, tBuMgCl, DMF

Step 1:—Preparation of Isopropyl ((((R)-1-(isopropyloxy)-1-oxopropan-2-yl)amino)(perfluoro-phenoxy)-phosphoryl)-L-alaninate 35

To a stirred solution of POCl₃ (0.360 mL, 3.81 mmol, 1 eq.) in CH₂Cl₂ (2.5 mL) under Ar cooled to −78° C. dropwise added isopropyl L-alaninate 35 (1.00 g, 7.62 mmol, 2 eq.) as a solution in CH₂Cl₂ (2.5 mL) maintaining temperature <−60° C. Et₃N (1.06 mL, 7.62 mmol, 2 eq.) was added dropwise maintaining temperature <−60° C. The mixture was stirred at −78° C. for 1 h, then warmed to 0° C. and stirred for 45 min. A pre-stirred mixture of pentafluorophenol (700 mg, 3.81 mmol, 1 eq.) and Et₃N (1.06 mL, 7.62 mmol, 2 eq.) in CH₂Cl₂ (4 mL) was added to the main reaction mixture, and stirred for 2 h at 0° C., and then at ambient temperature for 2 h. To the mixture was added SiO₂ (ca. 5 g) and EtOAc (50 mL). The reaction mixture was stirred for 5 min, and then filtered. The filter cake was washed with EtOAc (100 mL). The filtrate was concentrated in vacuo to give an oily solid. Purified by flash chromatography (SiO2, eluting 33-50% EtOAc/heptane) to give isopropyl ((((R)-1-(isopropyloxy)-1-oxopropan-2-yl)amino)-(perfluorophenoxy)phosphoryl)-L-alaninate, 36, (619 mg, 33% yield) as a white solid.

¹H NMR (CDCl₃, 300 MHz) $\delta_H$ 5.06 (septet, 2H), 4.07 (sept, 2H), 3.74 (q, 2H), 1.46 (d, 3H), 1.43 (d, 3H), 1.28 (d, 6H), 1.27 (d, 6H). ³¹P NMR (CDCl₃, 162 MHz) $\delta_P$ 10.70 (s).

Step 2: Preparation of Isopropyl (2S)-2-[[[(2S,3S,4R,5R)-5-(4-amino-2-oxo-pyrimidin-1-yl)-2,4-difluoro-3-hydroxy-4-methyl-tetrahydrofuran-2-yl]methoxy-[[(1S)-2-isopropoxy-1-methyl-2-oxo-ethyl]amino]phosphoryl]amino]propanoate I-6

To a stirred suspension of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (100 mg, 0.360 mmol, 1 eq.) in dry DMF (3 mL) under Argon at 0° C. was added ᵗBuMgCl (0.72 mL, 0.72 mmol, 2 eq., 1M in THF). To the mixture was added pentan-3-yl ((perfluorophenoxy)(phenoxy)phosphoryl)-L-alaninate 36 (690 mg, 0.72 mmol, 2 eq.) and the reaction mixture was stirred at 0° C. for 1.5 h. The reaction mixture was diluted with 2-MeTHF and added to NH₄Cl (sat. aq.) and water. The aqueous phase was extracted into 2-MeTHF. The combined organic phases were dried over MgSO₄, filtered and the concentrated in vacuo to give a brown oil. Purification by flash chromatography (SiO₂, eluting 10-15% MeOH/CH₂Cl₂) gave an off-white foam which was purified by MDAP (XSelect C18, eluting 20-40% MeCN/water). Fractions containing product freeze dried to give isopropyl (2S)-2-[[[(2S,3S,4R,5R)-5-(4-amino-2-oxo-pyrimidin-1-yl)-2,4-difluoro-3-hydroxy-4-methyl-tetrahydrofuran-2-yl]methoxy-[[(1S)-2-isopropoxy-1-methyl-2-oxo-ethyl]amino]phosphoryl]amino]propanoate, I-6, (24 mg, 11% yield) as a white solid.

¹H NMR (DMSO-d₆, 400 MHz) $\delta_H$ 7.33 (br s, 1H), 7.39 (d, 1H), 6.46 (d, 1H), 6.06 (d, 1H), 5.78 (d, 1H), 4.98 (q, 2H), 4.90-4.80 (m, 2H), 4.04 (br s, 3H), 3.77-3.65 (m, 2H), 1.22 (d, 6H), 1.17-1.13 (m, 5H). ¹⁹F NMR (DMSO-d₆, 376 MHz) $\delta_F$ −22.3 (t, 1F), −154.9 (sept, 1F)

³¹P NMR (DMSO-d₆, 161 MHz) $\delta_P$ 13.6 (s). UPLC (Acid, 2-95%, CSH C18) RT=1.687 min, 98.54 ESIneg m/z 582 [M-H]⁻

Example 6

Synthesis of Cyclohexyl (2S)-2-[[[(2S,3S,4R,5R)-5-(4-amino-2-oxo-pyrimidin-1-yl)-2,4-difluoro-3-hydroxy-4-methyl-tetrahydrofuran-2-yl]methoxy-[[(1S)-2-(cyclohexoxy)-1-methyl-2-oxo-ethyl]amino]phosphoryl]amino]propanoate, I-7

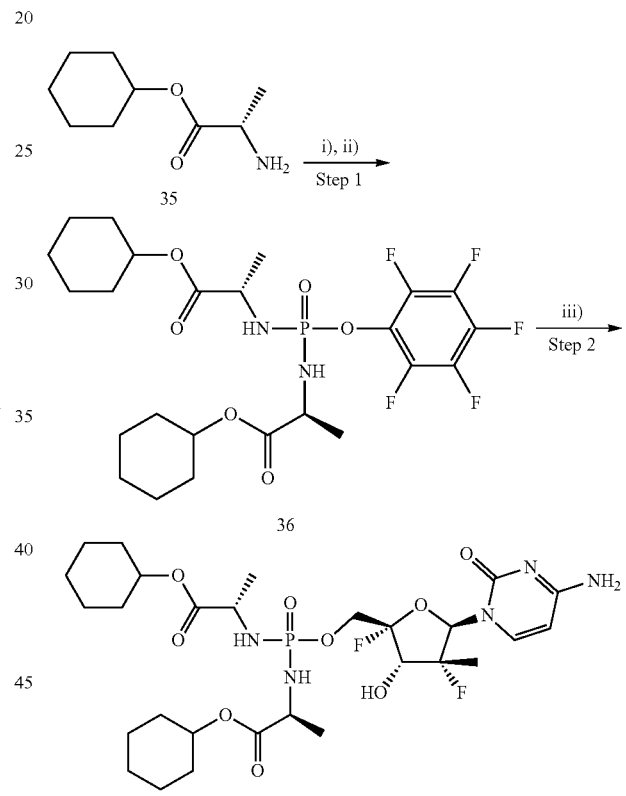

I-7 i) POCl₃, Et₃N, CH₂Cl₂; ; ii) C₆F₅OH, Et₃N, CH₂Cl₂ iv) 25, tBuMgCl, DMF

Step 1:—Preparation of Cyclohexyl ((((R)-1-(cyclohexyloxy)-1-oxopropan-2-yl)amino)(perfluorophenoxy)phosphoryl)-L-alaninate, 37

To a stirred solution of POCl₃ (303 µL, 3.25 mmol, 1 eq.) in CH₂Cl₂ (2 mL) under Ar cooled to −78° C. dropwise added cyclohexyl L-alaninate (1.11 g, 6.49 mmol, 2 eq.) as solution in CH₂Cl₂ (2 mL). Et₃N (0.902 mL, 6.49 mmol, 2 eq.) was added dropwise. The mixture was stirred at −78° C. for 1 h, then warmed to 0° C. and stirred for 30 min. A pre-stirred mixture of pentafluorophenol (657 mg, 3.57 mmol, 1.1 eq.) and Et₃N (0.902 mL, 6.49 mmol, 2 eq.) in CH₂Cl₂ (2 mL) was added to the main reaction mixture, and stirred for 2 h at 0° C. The mixture was concentrated in vacuo to give a white solid. The solid was suspended in EtOAc/heptane (2:3) and stirred with SiO$_2$. The mixture was filtered, and the filter cake washed with EtOAc/heptane (2:3). The filtrate was concentrated in vacuo to give a colorless oil. Purification by Isolera (SiO$_2$, 80 g ZIP SPHERE cartridge, eluting 12-100% EtOAc/heptanes) gave cyclohexyl ((((R)-1-(cyclohexyloxy)-1-oxopropan-2-yl)amino)(perfluorophenoxy)phosphoryl)-L-alaninate, 37, (250 mg, 25%) as a white solid. $^1$H NMR (CDCl$_3$, 400 MHz) $\delta_H$ 4.86-4.78 (m, 2H), 4.14-4.01 (m, 2H), 3.79-3.69 (m, 2H), 1.85-1.72 (m, 8H), 1.62-1.25 (m, 18H).

$^{19}$F NMR (DMSO-d$_6$, 376 MHz) $\delta_F$ −154 (d, 2F), −160 (t, 1F), −162 (d, 2F). $^{31}$P NMR (DMSO-d$_6$, 161 MHz) $\delta_p$ 10.7 (s).

Step 2: Preparation of Cyclohexyl (2S)-2-[[[(2S,3S,4R,5R)-5-(4-amino-2-oxo-pyrimidin-fluoro-3-hydroxy-4-m ethyl-tetrahydrofuran-2-yl]methoxy-[[(1S)-2-(cyclohexoxy)-1-methyl-2-oxo-ethyl]amino]phosphoryl]amino]propanoate, I-7

To a stirred solution of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (168 mg, 0.607 mmol, 1 eq.) in DMF (5 mL) under Argon at 0° C. was added $^t$BuMgCl (1.28 mL, 0.911 mmol, 2 eq., 1M in THF). The reaction mixture was stirred for 15 min at 0° C. to give a suspension. To this mixture was added cyclohexyl ((((R)-1-(cyclohexyloxy)-1-oxopropan-2-yl)amino)(perfluoro-phenoxy)phosphoryl)-L-alaninate (502 mg, 0.911 mmol, 1.5 eq.), and stirred for 2 h at 0° C. The mixture was added to NH$_4$Cl (30 mL, sat. aq.), and extracted into 2-MeTHF. The organic phases were combined and dried over MgSO$_4$, filtered and concentrated in vacuo. Purification by MDAP (XSelect C18, eluting 30-60% MeCN/water) gave cyclohexyl (2S)-2-[[[(2S,3S,4R,5R)-5-(4-amino-2-oxo-pyrimidin-1-yl)-2,4-difluoro-3hydroxy-4-methyl-tetrahydrofuran-2-yl]methoxy-[[(1S)-2-(cyclohexoxy)-1-methyl-2-oxo-ethyl]amino]phosphoryl]amino]propanoate, I-7, (58.5 mg, 15% yield) as a white solid. $^1$H NMR (DMSO-d$_6$ with D$_2$O, 400 MHz) $\delta_H$ 147.32 (d, 1H), 6.44 (d, 1H), 5.78 (d, 1H), 4.98 (d, 1H), 4.62 (d, 1H), 4.03 (m, 3H), 3.72 (m, 2H), 1.86-1.00 (m, 29H). $^{19}$F NMR (DMSO-d$_6$, 376 MHz) $\delta_F$ −122 (m, 1F) −155 (m, 1F). $^{31}$P NMR (DMSO-d$_6$, 161 MHz) $\delta_p$ 13.6 (s). UPLC (Neutral, 2-95%, CSH C18) RT=2.377 min, 99.5% ESIpos m/z 664 MH$^+$ Example 7

Synthesis of ((2S,3S,4R,5R)-5-(4-amino-2-oxopyrimidin-1(2H)-yl)-2,4-difluoro-3-hydroxy-4-methyl-tetrahydrofuran-2-yl)methyl Diphenyl Phosphate, I-8

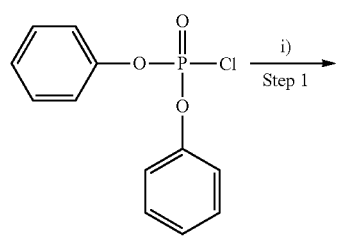

38

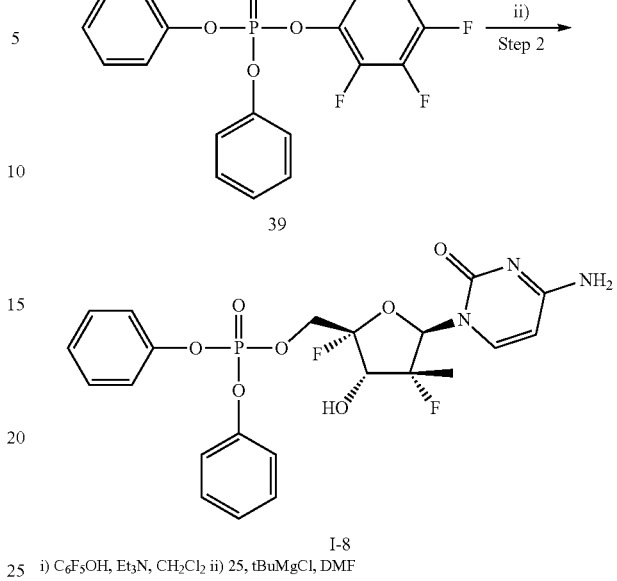

i) C$_6$F$_5$OH, Et$_3$N, CH$_2$Cl$_2$ ii) 25, tBuMgCl, DMF

Step 1: Preparation of Perfluorophenyl Diphenyl Phosphate, 39

To a stirred solution of pentafluorophenol (2 g, 10.9 mmol, 1 eq.), and Et$_3$N (3.79 mL, 27.2 mmol) in CH$_2$Cl$_2$ at 0° C. under Ar was added diphenyl phosphorochloridate 38 (2.70 mL, 13.0 mmol, 1.2 eq.). The mixture was stirred at 0° C. for 1 h, and then at ambient temperature for 16 h. The reaction mixture was concentrated in vacuo. The resulting oil was suspended in EtOAc and washed with water and brine, dried over MgSO$_4$, filtered and concentrated in vacuo to give perfluorophenyl diphenyl phosphate, 39, (4.23 g, 94% yield) as a pale brown oil. $^1$H NMR (CDCl$_3$, 300 MHz) $\delta_H$ 7.42-7.35 (m, 5H), 7.32-7.24 (m, 5H). $^{31}$P NMR (CDCl$_3$, 161 MHz) $\delta_p$ −16.4 (s). UPLC (Acid, 2-95%, CSH C18) RT=2.377 min ESIpos m/z 417 MH$^+$ Step 2: Preparation of ((2S,3S,4R,5R)-5-(4-amino-2-oxopyrimidin-1(2H)-yl)-2,4-difluoro-3-hydroxy-4-methyltetrahydrofuran-2-yl)methyl Diphenyl Phosphate, I-8

To a stirred suspension of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (150 mg, 0.54 mmol, 1 eq.) and perfluorophenyl diphenyl phosphate (270 mg, 0.65 mmol) in dry MeCN added 1-methylimidazole (0.22 mL, 2.71 mmol, 5 eq.) at ambient temperature and stirred for 3 h. The reaction mixture was added to EtOAc and brine. The phases were separated, and the aqueous phase extracted with EtOAc. The combined organic layers were dried over MgSO$_4$, filtered and concentrated in vacuo to give a brown oil. Purification by flash chromatography (SiO$_2$, eluting 10-15% MeOH/CH$_2$Cl$_2$), followed by purification by MDAP (XSelect C18, eluting 30-60% MeCN/water) gave ((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate, I-8 (9.5 mg, 3.5% yield) as a white solid. $^1$H NMR (DMSO-d$_6$, 300 MHz) $\delta_H$ 7.38/7.23-7.20 (br m, 13H), 6.48/6.27/5.90-5.64 (3H, m), 4.59 (br s, 1H), 4.47/4.06 (br t, 1H), 1.03/1.17 (br d, 3H) (rotameric). $^{19}$F NMR (DMSO-$d_6$, 283 MHz) $\delta_F$ −120.0/−12.8 (m, 1F), −148.9/−154.1 (m, 1F). $^{31}$P NMR (DMSO-$d_6$, 161 MHz) $\delta_P$ −11.5. UPLC (Acid, 2-95%, CSH C18) RT=1.43 min, 97.21% ESIneg m/z 508 [M-H]$^{31}$

Example 8

Synthesis of Isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate, I-9

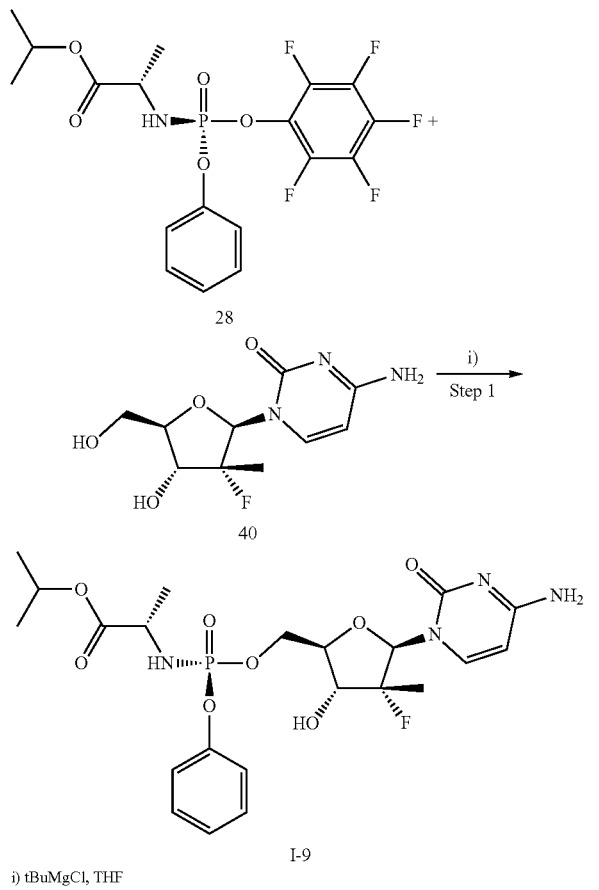

i) tBuMgCl, THF

Step 1: Preparation of Isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate, I-9

To a stirred mixture 4-amino-1-((2R,3R,4R,5R)-3-fluoro-4-hydroxy-5-(hydroxymethyl)-3-methyltetrahydrofuran-2-yl)pyrimidin-2(1H)-one-methane 40 (301 mg, 1.77 mmol, 1 eq.) in dry THF (10 mL) under Argon at 0° C. was added $^t$BuMgCl (1.75 mL, 1.75 mmol, 1.5 eq., 1M in THF). The mixture was stirred for 15 min at 0° C., and isopropyl ((S)-(perfluorophenoxy-) (phenyl)phosphoryl)-L-alaninate (793 mg, 1.75 mmol, 1.5 eq.) added. The mixture was stirred for 1 h at 0° C. The mixture was added to NH$_4$Cl (sat. aq.) and extracted into EtOAc. The organic phase was washed with Na$_2$HCO$_3$ (sat. aq.), brine ( ), dried over MgSO$_4$, filtered and concentrated in vacuo at 40° C. The crude product was purified by HPLC (XSelect C18, eluting 25-30% MeCN/water). Fractions containing product were combined and freeze dried to give isopropyl ((S)-(((2R,3R,4R,5R)-5-(4-amino-2-oxopyrimidin-1(2H)-yl)-4-fluoro-3-hydroxy-4-methyltetrahydrofuran-2-yl)methoxy)(phenoxy)phosphoryl)-L-alaninate, I-9 (137 mg, 30% yield) as a white solid. $^1$H NMR (DMSO-$d_6$ with D$_2$O, 400 MHz) $\delta_H$ 7.51-7.03 (m, 6H), 6.08 (br m, 1H), 5.68 (d, 1H), 4.79 (m, 1H), 4.18 (m, 1H), 3.94 (m, 1H), 3.81-3.62 (m, 2H), 1.24-1.02 (m, 12H). $^{19}$F NMR (DMSO-$d_6$, 376 MHz) $\delta_F$ −159 (m, 1F). $^{31}$P NMR (DMSO-$d_6$, 161 MHz) $\delta_P$ 4.42 (s). UPLC (Neutral, 2-95%, CSH C18) RT=1.763 min, 100% ESIpos m/z 279 MH$^+$

Example 9

Synthesis of ((2S,3S,4R,5R)-5-(4-amino-2-oxopyrimidin-1(2H)-yl)-2,4-difluoro-3-hydroxy-4-methyltetrahydrofuran-2-yl)methyl (4-methoxybenzyl) phosphordiamidate, I-10

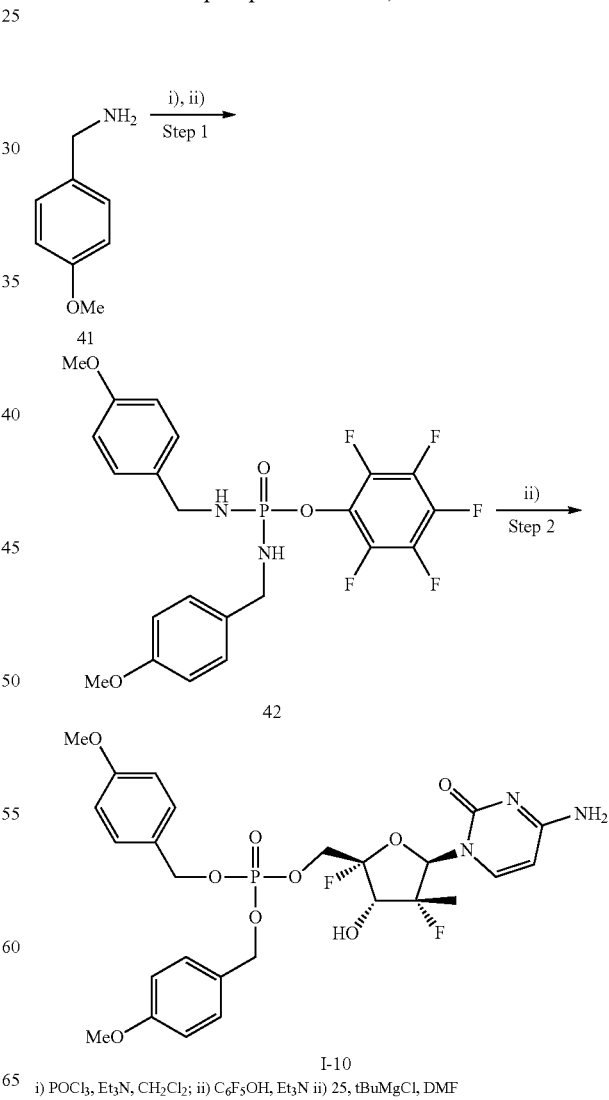

i) POCl$_3$, Et$_3$N, CH$_2$Cl$_2$; ii) C$_6$F$_5$OH, Et$_3$N ii) 25, tBuMgCl, DMF

Step 1: Preparation 4-methoxybenzyl (perfluorophenyl) Phosphordiamidate, 41

A solution of phosphorous(V) oxychloride (609 μL, 6.52 mmol, 1 eq.) under Ar in $CH_2Cl_2$ was cooled to −78° C. To the mixture was added dropwise 4-methoxybenzylamine (1.70 mL, 13.0 mmol, 2 eq.) and then triethylamine (2.73 mL, 19.6 mmol). The mixture was stirred at −78° C. for 1 h, then warmed to 0° C. Pentafluorophenol (1.80 g, 9.78 mmol, 1.5 eq.) added. The mixture was warmed to ambient temperature over 1 h. The mixture was concentrated in vacuo to give a yellow solid. Purification by Isolera ($SiO_2$, 80 g ZIP SPHERE cartridge, eluting 0-50% EtOAc/heptanes) gave 4-methoxybenzyl (perfluorophenyl) phosphordiamidate, 41, as a white solid (2.00 g, 61% yield). $^1H$ NMR ($CDCl_3$, 400 MHz) $\delta_H$ 7.23 (m, 4H), 6.85 (m, 4H), 4.18 (m, 4H), 3.78 (s, 6H). $^{31}P$ NMR (DMSO-$d_6$, 161 MHz) $\delta_p$ 13.4 (s).

Step 2: Preparation of ((2S,3S,4R,5R)-5-(4-amino-2-oxopyrimidin-1(2H)-yl)-2,4-difluoro-3-hydroxy-4-methyltetrahydrofuran-2-yl)methyl (4-methoxybenzyl)phosphordiamidate, I-10

To a stirred mixture of 4-amino-1-((2R,3R,4S,5S)-3,5-difluoro-4-hydroxy-5-(hydroxymethyl)-3-methyltetrahydrofuran-2-yl)pyrimidin-2(1H)-one 25 (200 mg, 0.721 mmol, 1 eq.) in dry THF (10 mL) under Ar at 0° C. was added $^t$BuMgCl (1.08 mL, 1.44 mmol, 1.5 eq., 1M in THF). The mixture was stirred for 15 min at 0° C., and 4-methoxybenzyl (perfluorophenyl) phosphordiamidate (495 mg, 1.08 mmol, 1.5 eq.) added. The mixture was stirred for 1 h at 0° C. The mixture was added to $NH_4Cl$ (sat. aq.) and extracted into EtOAc. The organic phase was washed with $Na_2HCO_3$ (sat. aq.), brine ( ), dried over $MgSO_4$, filtered and concentrated in vacuo at 40° C. This was repeated on an equivalent scale, and the crude materials combined and purified by MDAP (XSelect C18, eluting MeCN/water). Fractions containing product were combined and freeze dried to give ((2S,3S,4R,5R)-5-(4-amino-2-oxopyrimidin-1(2H)-yl)-2,4-difluoro-3-hydroxy-4-methyltetrahydrofuran-2-yl)methyl (4-methoxybenzyl)phosphordiamidate, I-10, as a white solid (113 mg, 13% yield). $^1H$ NMR (DMSO-$d_6$ with $D_{20}$, 300 MHz) $\delta_H$ 7.27 (d, 1H), 7.19 (m, 4H), 6.81 (m, 4H), 6.43 (d, 1H), 5.70 (d, 1H), 5.10 (m, 1H), 4.10-3.77 (m, 6H), 3.60 (s, 6H), 1.14 (d, 3H). $^{19}F$ NMR (DMSO-$d_6$, 376 MHz) $\delta_F$ −122 (m, 1F) −155 (m, 1F) $^{31}P$ NMR (DMSO-$d_6$, 161 MHz) $\delta_p$ 17.1 (s). UPLC (Neutral, 2-95%, CSH C18) RT=1.795 min, 99.6% ESIpos m/z 595 $MH^+$

BIOLOGICAL EXAMPLES

HCV Replicon Assay

This assay measures the ability of the compounds of Formula I to inhibit HCV RNA replication, and therefore their potential utility for the treatment of HCV infections. The assay utilizes a reporter as a simple readout for intracellular HCV replicon RNA level. The *Renilla luciferase* gene is introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA is electroporated into human hepatoma Huh7 cells, and G418-resistant colonies are isolated and expanded. Stably selected cell line 2209-23 contains replicative HCV subgenomic RNA, and the activity of *Renilla luciferase* expressed by the replicon reflects its RNA level in the cells. The assay is carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, are cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium are added to the cells, which are then further incubated at 37° C. for three days. At the end of the incubation time, the cells in white plates are harvested and luciferase activity is measured by using the *R. luciferase* Assay system (Promega cat no. E2820). All the reagents described in the following paragraph are included in the manufacturer's kit, and the manufacturer's instructions are followed for preparations of the reagents. The cells are washed once with 100 μL of phosphate buffered saline (pH 7.0) (PBS) per well and lysed with 20 μl of 1× *R. luciferase* Assay lysis buffer prior to incubation at room temperature for 20 min. The plate is then inserted into the Centro LB 960 microplate luminometer (Berthold Technologies), and 100 μl of *R. luciferase* Assay buffer is injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) is used for the cytotoxicity assay. Ten microliter of WST-1 reagent is added to each well of the transparent plates including wells that contain media alone as blanks. Cells are then incubated for 2 h at 37° C., and the OD value is measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

Combination Therapy Assays Protocols and Results

Methods

1. Cell Culture Medium

DMEM Growth Medium contains Dulbecco's Modification of Eagle's Medium (DMEM) supplemented with 10% heat-inactivated fetal bovine serum (FBS), 1×MEM non-essential amino acids, 2 mM L-glutamine, 100 IU/ml penicillin and 100 µg/ml *streptomycin*.

HCV Replicon Assay Medium contains DMEM-Phenol Red Free supplemented with 5% heat-inactivated FBS, 1×MEM non-essential amino acids, 2 mM L-glutamine, 100 IU/ml penicillin and 100 µg/ml streptomycin.

2. Cell Culture

HCV 1b replicon cells, which express a bicistronic genotype 1b replicon in Huh7-Lunet cells, were cultured at 37° C. with 5% $CO_2$ in DMEM Growth Medium plus 250 µg/ml G418.

3. Antiviral Combination Assays

HCV inhibitor combination assays were performed in HCV 1b replicon cells. HCV 1b replicon cells were seeded at the density of 4000 cells/well/100 µl in 96-well flat-bottom white plates 24 hrs prior to the compound treatment. For the drug combination studies, compound stock solutions (1.75 mM isopropyl ((S)-(((2S,3S,4R,5R)-5-(2,4-dioxo-3,4-dihydropyrimidin-1(2H)-yl)-2,4-difluoro-3-hydroxy-4-methyltetrahydrofuran-2-yl)methoxy)(naphthalen-1-yloxy)phosphoryl)-L-alaninate compound II-1 and 1 mM isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate, compound I-1 in 100% DMSO) were diluted 100-fold in replicon assay medium, yielding 17.5 µM II-1 and 10 µM I-1 in 1% DMSO, respectively. Both compounds were then serially diluted 1.5-fold in replicon assay medium with 1% DMSO to obtain 10-time concentrated range of concentrations −1.75-0.068 µM for II-1 and 1-0.088 µM for I-1, respectively. 12.5 µl of these 10-time concentrated serial dilution of II-1 (Horizontal drug) and 12.5 µl of I-1 (Vertical drug) were added to the replicon cells. The final concentration of DMSO in the cell culture medium for all testing points were 0.2%. Three days after the treatment, the antiviral activities were determined by measuring replicon luciferase activity by adding 70 µl/well of One-Glo® reagent (Promega). The relative light units (RLU) were measured using a Perkin Elmer EnSpire reader set to read for 0.5 sec/well. The drug treatment scheme for compound II-1 and compound I-1 in combination were generated using the template shown in Table A 4. Data Analysis Data were analyzed using the MacSynergy™ II program developed by Prichard and Shipman. The combination effect of each pair of inhibitors was calculated by the volume of surface deviations (volumes are expressed as µM concentration times µM concentration times percentage, or $\mu M^2\%$) at 95% confidence, Bonferroni Adjusted.

TABLE A

Compound Treatment Template for Combination Studies

| Vertical drug | | Horizontal drug II-1 Concentration ranges [µM] | | | | | | | | | | | |
|---|---|---|---|---|---|---|---|---|---|---|---|---|---|
| I-1 | | 0 | 0.068 | 0.102 | 0.154 | 0.230 | 0.346 | 0.519 | 0.778 | 1.167 | 1.75 | | |
| Concentration ranges [µM] | 1 | X | X | X | X | X | X | X | X | X | X | VC | CC |
| | 0.667 | X | X | X | X | X | X | X | X | X | X | VC | CC |
| | 0.444 | X | X | X | X | X | X | X | X | X | X | VC | CC |
| | 0.296 | X | X | X | X | X | X | X | X | X | X | VC | CC |
| | 0.198 | X | X | X | X | X | X | X | X | X | X | VC | CC |
| | 0.132 | X | X | X | X | X | X | X | X | X | X | VC | CC |
| | 0.088 | X | X | X | X | X | X | X | X | X | X | VC | CC |
| | 0 | X | X | X | X | X | X | X | X | X | X | VC | CC |

VC: vehicle control (0.2% DMSO)
CC: cell control (no cells, replicon assay medium only)

Results

| Drug 1 | Drug 2 | Synergy | Antagonism | Nuc Combo | Max % I | Min % I | Max % SD | Min % SD |
|---|---|---|---|---|---|---|---|---|
| Sofosbuvir (II-3) | Sofosbuvir (II-3) | 11 | −6.5 | additive | U:U | 100 | 42.85 | 4.57 | 0 |
| II-1 | Sofosbuvir (II-3) | 8.7 | −9.2 | additive | U:U | 100 | 31.56 | 6.23 | 0 |
| II-1 | Sofosbuvir (II-3) | 59 | −11 | mod syn | U:U | 99.9 | 24.62 | 9.66 | 0 |
| II-1 | I-1 | 115 | −10 | strong syn | U:C | 99.8 | 5.43 | 6.14 | 0 |
| II-1 | I-1 | 66 | −12 | mod syn | U:C | 99.7 | 3.78 | 13.37 | 0.01 |
| Sofosbuvir (II-3) | I-1 | 59 | −15 | mod syn | U:C | 99.9 | 9.2 | 11.08 | 0.01 |
| Sofosbuvir (II-3) | I-1 | 815 | −1.6 | strong syn | U:C | 99.5 | −2.12 | 9.49 | 0 |
| Sofosbuvir (II-3) | I-1 | 238 | −32 | strong syn | U:C | 99.8 | −4.15 | 11.93 | 0.03 |
| II-1 | I-1 | 309 | −5.2 | strong syn | U:C | 99.3 | −9.15 | 15.72 | 0.01 |
| II-1 | I-1 | 143 | −25 | strong syn | U:C | 99.7 | 10.79 | 8.02 | 0 |
| II-1 | I-3 | 148 | −8.3 | strong syn | U:C | 99.5 | −2.07 | 12.35 | 0.03 |

As seen above, the cytidine nucleoside analogues of Formula I, in combination with the uridine nucleoside analogues of Formula II, produce a synergistic effect on the inhibition of HCV polymerase.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A method of treatment of HCV comprising administering to a patient in need thereof, a combination of a compound of Formula I and a compound of Formula II:

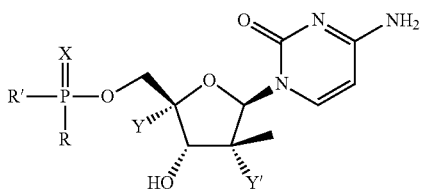

wherein:
R in Formula I is O—$R^1$ or $NHC(R^{2a})(R^{2b})C(=O)OR^3$;
R' in Formula I is O—$R^1$ or $NHC(R^{2a})(R^{2b})C(=O)OR^3$;
each $R^1$ in Formula I is independently phenyl or naphthyl, optionally substituted with one or more lower alkyl, lower alkoxy, halo, lower haloalkyl, or cyano;
each $R^{2a}$ and $R^{2b}$ in Formula I are independently H or lower alkyl;
each $R^3$ in Formula I is independently H, lower alkyl, lower haloalkyl, cycloalkyl, phenyl or phenyl lower alkyl;
X in Formula I is O or S;
Y in Formula I is F; and
Y' in Formula I is F or OH;
or a pharmacologically acceptable salt thereof; and

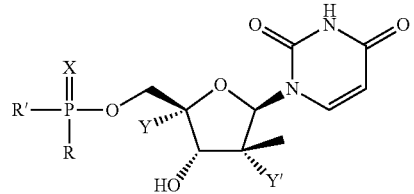

wherein:
R in Formula II is O—$R^1$ or $NHC(R^{2a})(R^{2b})C(=O)OR^3$;
R' in Formula II is O—$R^1$ or $NHC(R^{2a})(R^{2b})C(=O)OR^3$;
each $R^1$ in Formula II is independently phenyl or naphthyl, optionally substituted with one or more lower alkyl, lower alkoxy, halo, lower haloalkyl, or cyano;
each $R^{2a}$ and $R^{2b}$ in Formula II are independently H or lower alkyl;
each $R^3$ in Formula II is independently H, lower alkyl, lower haloalkyl, cycloalkyl, phenyl or phenyl lower alkyl;
X in Formula II is O or S;
Y in Formula II is H or F; and
Y' in Formula II is F or OH;
or a pharmacologically acceptable salt thereof.

2. The method of claim 1 wherein:
each $R^3$ in Formula I or Formula II is independently H, lower alkyl, lower haloalkyl, phenyl or phenyl lower alkyl;
or a pharmacologically acceptable salt thereof.

3. The method of claim 1, wherein wherein the compound of Formula I is selected from the group consisting of:
isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;
isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;
isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
pentan-3-yl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;
dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;
((2S,3S,4R,5R)-5-(4-amino-2-oxopyrimidin-1(2H)-yl)-2,4-difluoro-3-hydroxy-4-methyltetrahydrofuran-2-yl) methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;
cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;
dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;
pentan-3-yl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;
((2S,3S,4R,5R)-5-(4-amino-2-oxopyrimidin-1(2H)-yl)-2-fluoro-3,4-dihydroxy-4-methyltetrahydrofuran-2-yl) methyl diphenyl phosphate;
isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;
isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate;
isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
cyclohexyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
pentan-3-yl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;
cyclohexyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;
pentan-3-yl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;
isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate; and
isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate;

or a mixture of $S_P$ and $R_P$ epimers thereof; or a pharmaceutically acceptable salt thereof of each of the foregoing compounds.

4. The method of claim 2, wherein the compound of Formula I is:

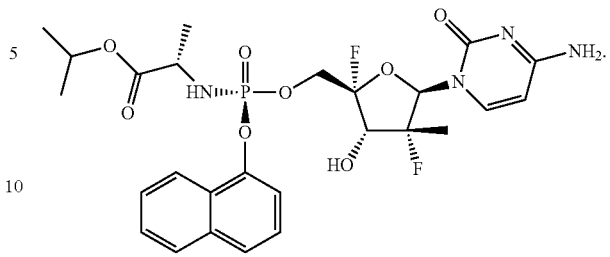

5. The method of claim 2, wherein the compound of Formula I is:

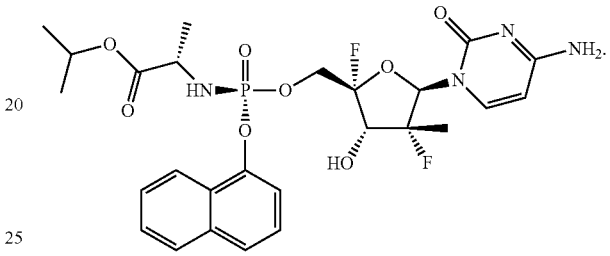

6. The method of claim 2, wherein the compound of Formula I is:

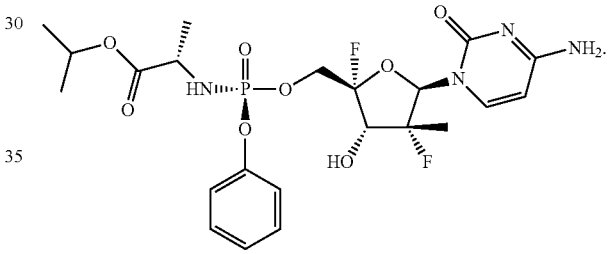

7. The method of claim 2, wherein the compound of Formula II is:

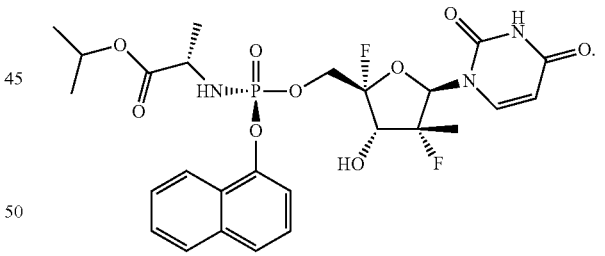

8. The method of claim 2, wherein the compound of Formula II is:

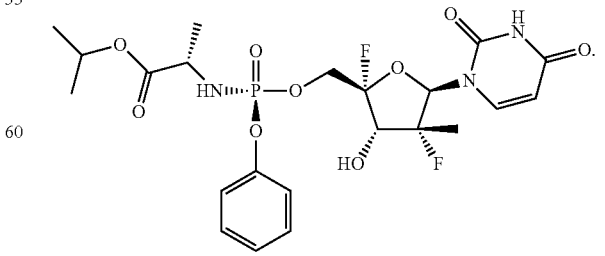

9. The method of claim 2, wherein the compound of Formula II is:

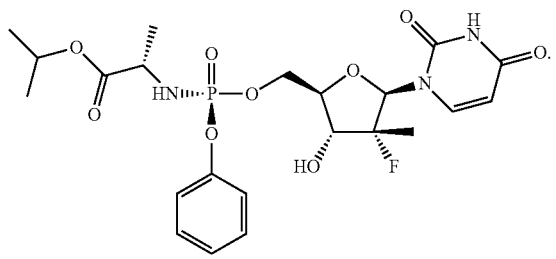

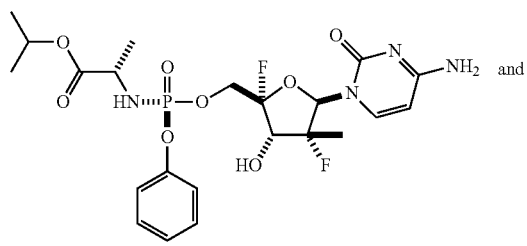

10. The method of claim 2, wherein the compound of Formula I and the compound of Formula II are, respectively,

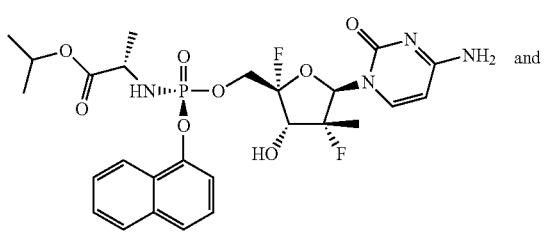

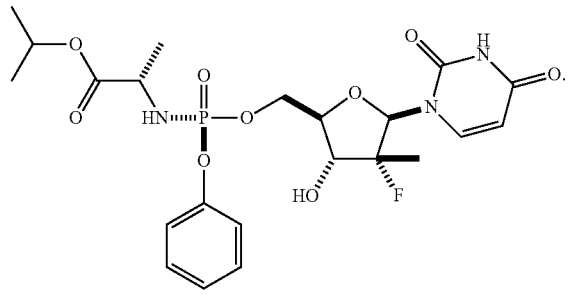

13. The method of claim 2, wherein the compound of Formula I and the compound of Formula II are, respectively,

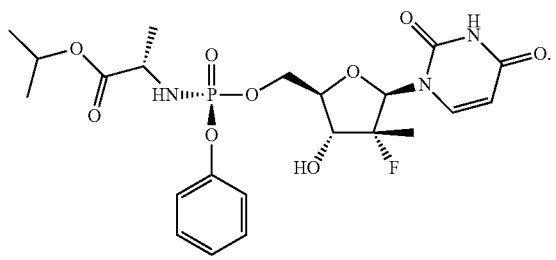 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

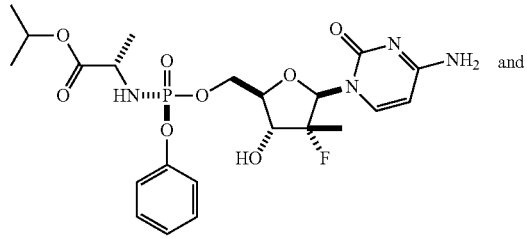

11. The method of claim 2, wherein the compound of Formula I and the compound of Formula II are, respectively,

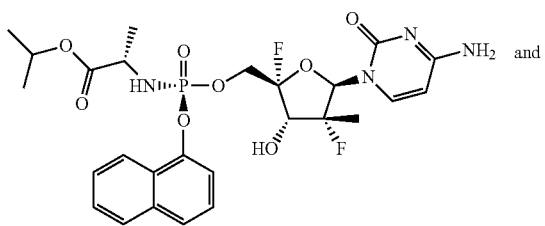

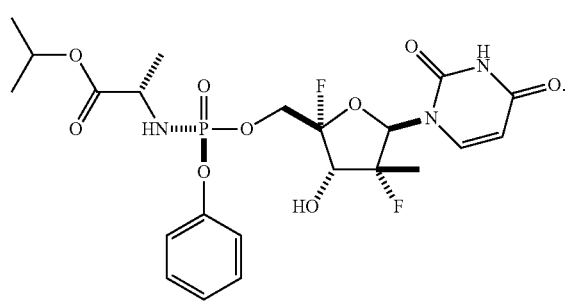

14. The method of claim 2, wherein the compound of Formula I and the compound of Formula II are, respectively,

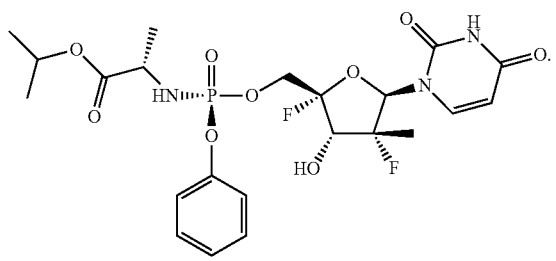

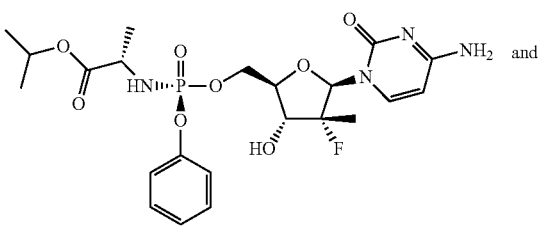

12. The method of claim 2, wherein the compound of Formula I and the compound of Formula II are, respectively, -continued

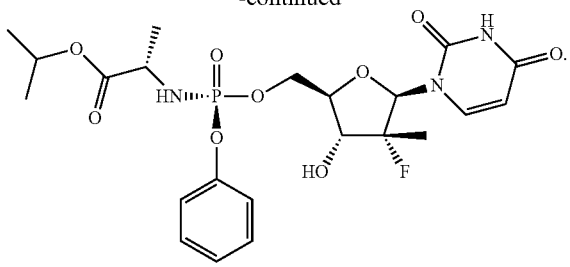

15. The method of claim 2, wherein the combination of a compound of Formula I and a compound of Formula II further comprises one or more of ribavirin, peginterferon-α, simeprevir, ledipasvir, daclatasvir, and velpatasvir.

16. A composition comprising a compound of Formula I and a compound of Formula II, admixed with at least one carrier, diluent or excipient

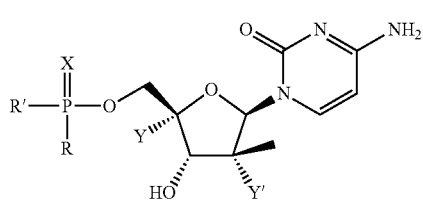

wherein:
  R in Formula I is O—$R^1$ or NHC($R^{2a}$)($R^{2b}$)C(=O)O$R^3$;
  R' in Formula I is O—$R^1$ or NHC($R^{2a}$)($R^{2b}$)C(=O)O$R^3$;
    each $R^1$ in Formula I is independently phenyl or naphthyl, optionally substituted with one or more lower alkyl, lower alkoxy, halo, lower haloalkyl, or cyano;
    each $R^{2a}$ and $R^{2b}$ in Formula I are independently H or lower alkyl;
    each $R^3$ in Formula I is independently H, lower alkyl, lower haloalkyl, cycloalkyl, phenyl or phenyl lower alkyl;
  X in Formula I is O or S;
  Y in Formula I is F; and
  Y' in Formula I is F or OH;
or a pharmacologically acceptable salt thereof; and

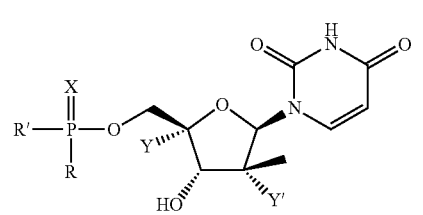

wherein:
  R in Formula II is O—$R^1$ or NHC($R^{2a}$)($R^{2b}$)C(=O)O$R^3$;
  R' in Formula II is O—$R^1$ or NHC($R^{2a}$)($R^{2b}$)C(=O)O$R^3$;
    each $R^1$ in Formula II is independently phenyl or naphthyl, optionally substituted with one or more lower alkyl, lower alkoxy, halo, lower haloalkyl, or cyano;
    each $R^{2a}$ and $R^{2b}$ in Formula II are independently H or lower alkyl;
    each $R^3$ in Formula II is independently H, lower alkyl, lower haloalkyl, cycloalkyl, phenyl or phenyl lower alkyl;
  X in Formula II is O or S;
  Y in Formula II is H or F; and
  Y' in Formula II is F or OH;
or a pharmacologically acceptable salt thereof.

17. The composition of claim 16 wherein each $R^3$ in Formula I or Formula II is independently H, lower alkyl, lower haloalkyl, phenyl or phenyl lower alkyl.

18. A method of treatment of HCV by administering to a patient in need thereof a compound of Formula I and a compound of Formula II, further in combination with a NS3A HCV protease inhibitor

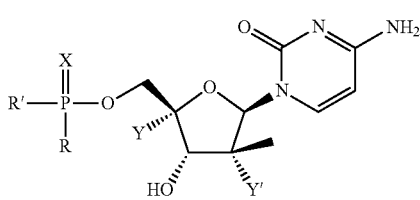

wherein:
  R in Formula I is O—$R^1$ or NHC($R^{2a}$)($R^{2b}$)C(=O)O$R^3$;
  each R' in Formula I is O—$R^1$ or NHC($R^{2a}$)($R^{2b}$)C(=O)O$R^3$;
    each $R^1$ in Formula I is independently phenyl or naphthyl, optionally substituted with one or more lower alkyl, lower alkoxy, halo, lower haloalkyl, or cyano;
    each $R^{2a}$ and $R^{2b}$ in Formula I are independently H or lower alkyl;
    each $R^3$ in Formula I is independently H, lower alkyl, lower haloalkyl, cycloalkyl, phenyl or phenyl lower alkyl;
  X in Formula I is O or S;
  Y in Formula I is F; and
  Y' in Formula I is F or OH;
or a pharmacologically acceptable salt thereof; and

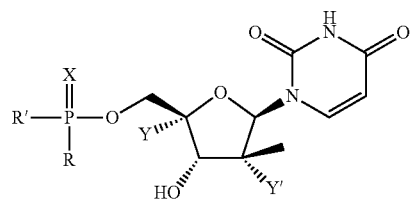

wherein:
  R in Formula II is O—$R^1$ or NHC($R^{2a}$)($R^{2b}$)C(=O)O$R^3$;
  R' in Formula II is O—$R^1$ or NHC($R^{2a}$)($R^{2b}$)C(=O)O$R^3$;

each R¹ in Formula II is independently phenyl or naphthyl, optionally substituted with one or more lower alkyl, lower alkoxy, halo, lower haloalkyl, or cyano;

each $R^{2a}$ and $R^{2b}$ in Formula II are independently H or lower alkyl;

each R³ in Formula II is independently H, lower alkyl, lower haloalkyl, cycloalkyl, phenyl or phenyl lower alkyl;

X in Formula II is O or S;

Y in Formula II is H or F; and

Y' in Formula II is F or OH;

or a pharmacologically acceptable salt thereof.

19. The method of claim 18 wherein each R³ in Formula I or Formula II is independently H, lower alkyl, lower haloalkyl, cycloalkyl, phenyl or phenyl lower alkyl.

20. A method of treatment of HCV by administering to a patient in need thereof a compound of Formula I and a compound of Formula II, further in combination with an additional NS5B HCV polymerase inhibitor

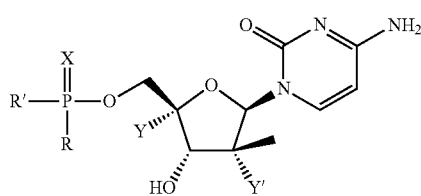

wherein:

R in Formula I is O—R¹ or $NHC(R^{2a})(R^{2b})C(=O)OR^3$;

each R' in Formula I is O—R¹ or $NHC(R^{2a})(R^{2b})C(=O)OR^3$;

each R¹ in Formula I is independently phenyl or naphthyl, optionally substituted with one or more lower alkyl, lower alkoxy, halo, lower haloalkyl, or cyano;

each $R^{2a}$ and $R^{2b}$ in Formula I are independently H or lower alkyl;

each R³ in Formula I is independently H, lower alkyl, lower haloalkyl, cycloalkyl, phenyl or phenyl lower alkyl;

X in Formula I is O or S;

Y in Formula I is F; and each Y' in Formula I is F or OH;

or a pharmacologically acceptable salt thereof; and

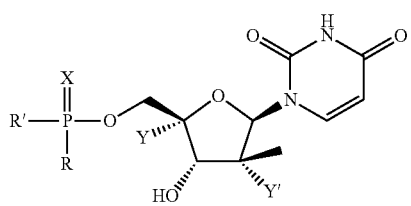

wherein:

R in Formula II is O—R¹ or $NHC(R^{2a})(R^{2b})C(=O)OR^3$;

R' in Formula II is O—R or $NHC(R^{2a})(R^{2b})C(=O)OR^3$;

each R¹ in Formula II is independently phenyl or naphthyl, optionally substituted with one or more lower alkyl, lower alkoxy, halo, lower haloalkyl, or cyano;

each $R^{2a}$ and $R^{2b}$ in Formula II are independently H or lower alkyl;

each R³ in Formula II is independently H, lower alkyl, lower haloalkyl, cycloalkyl, phenyl or phenyl lower alkyl;

X in Formula II is O or S;

Y in Formula II is H or F; and

Y' in Formula II is F or OH;

or a pharmacologically acceptable salt thereof.

21. The method of claim 20 wherein each R³ in Formula I or Formula II is independently H, lower alkyl, lower haloalkyl, cycloalkyl, phenyl or phenyl lower alkyl.

22. The method of claim 20, wherein the compound of Formula I is selected from the group consisting of:

isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate;

isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

pentan-3-yl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate;

((2S,3S,4R,5R)-5-(4-amino-2-oxopyrimidin-1(2H)-yl)-2,4-difluoro-3-hydroxy-4-methyltetrahydrofuran-2-yl) methyl diphenyl phosphate;

diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate;

pentan-3-yl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate;

isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate;

isopropyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

pentan-3-yl ((R)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate;

cyclohexyl ((R)-((2S,3S,4R,5R)-5-(4-amino-2-oxopyrimidin-1-(2H)-yl)-2-fluoro-3,4-dihydroxy-4-methyltetrahydrofuran-2-yl)methoxy)(phenoxy)phosphoryl)-L-alaninate;

pentan-3-yl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate;

isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate; and isopropyl ((R)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate;

or a mixture of $S_P$ and $R_P$ epimers thereof; or a pharmaceutically acceptable salt thereof of each of the foregoing compounds.

* * * * *